United States Patent [19]

Fitzgerald et al.

[11] 4,125,235

[45] Nov. 14, 1978

[54] APPARATUS FOR OPENING AN AIRCRAFT DOOR AND FOR ARMING AND DISARMING AN ESCAPE SLIDE DEPLOYING MECHANISM

[75] Inventors: James T. Fitzgerald, Mercer Island; Burton Bergman, Kent, both of Wash.

[73] Assignees: The Boeing Company, Seattle, Wash.; Aeritalia S.p.A., Naples, Italy

[21] Appl. No.: 784,568

[22] Filed: Apr. 4, 1977

[51] Int. Cl.² .............................................. B67C 1/14
[52] U.S. Cl. .................................. 244/129.5; 49/221; 49/360; 49/449; 244/137 P; 244/DIG. 2
[58] Field of Search ........... 244/137 R, 137 P, 118 R, 244/118 P, 129.1, 129.4, 129.5, 129.6, DIG. 2; 49/209, 210, 213, 216, 217, 221–224, 256, 199, 360, 361, 40, 197, 225, 322, 449; 296/146

[56] References Cited

U.S. PATENT DOCUMENTS

| | | | |
|---|---|---|---|
| 3,778,933 | 12/1973 | Nagy | 49/449 |
| 3,802,125 | 4/1974 | Baker | 49/360 |
| 3,852,854 | 12/1974 | Sigrud et al. | 244/137 P X |

*Primary Examiner*—Barry L. Kelmachter
*Attorney, Agent, or Firm*—Christensen, O'Connor, Johnson & Kindness

[57] ABSTRACT

An escape slide container is mounted for selective, upward movement with a track-mounted, overhead sliding door in an aircraft fuselage. Slide deployment mechanism for releasing the container from the door and for attaching it to the floor of the aircraft allows the door to move upwardly independently of the container, leaving the container attached to the floor. An over-center linkage supports the container above the floor while upward movement of the door trips the over-center linkage to propel the container outwardly through the door opening to deploy the escape slide under the urging of gravity. Apparatus for arming and disarming the slide for deployment operates in conjunction with door opening and closing apparatus that simultaneously effects movement of a door carrier to unplug the aircraft door from the opening in the fuselage and initiates upward traverse of the door along a plurality of tracks from which the door is supported at three points. Upon movement of a manually-actuated lever in a first direction, the door is unplugged and is opened. Upon movement of the same lever in the opposite direction, the door is closed, plugged in the door opening in the fuselage. Depending upon the position of a second manually-actuated lever, the slide either rises with the door or is deployed through the fuselage opening.

16 Claims, 38 Drawing Figures

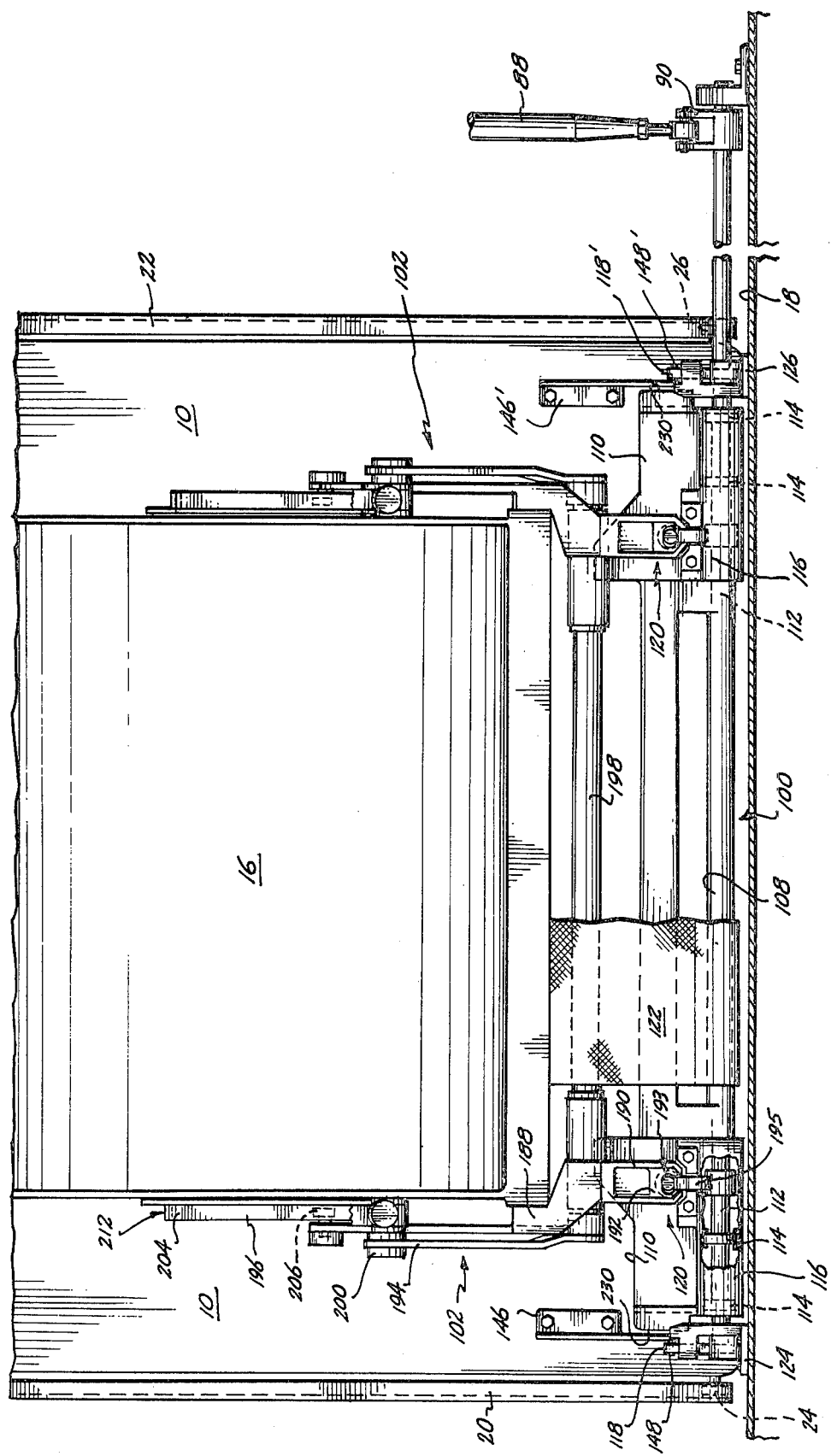

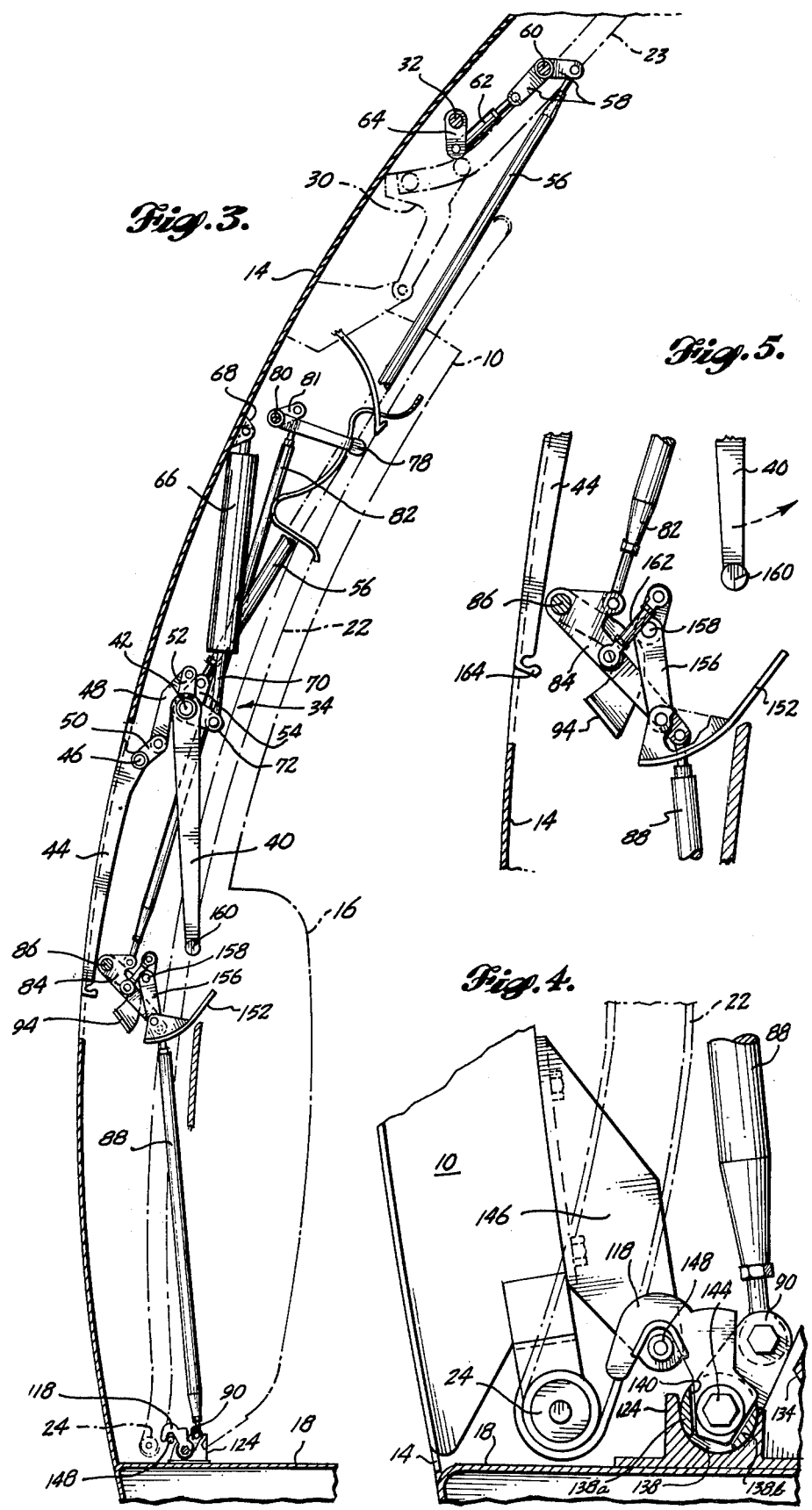

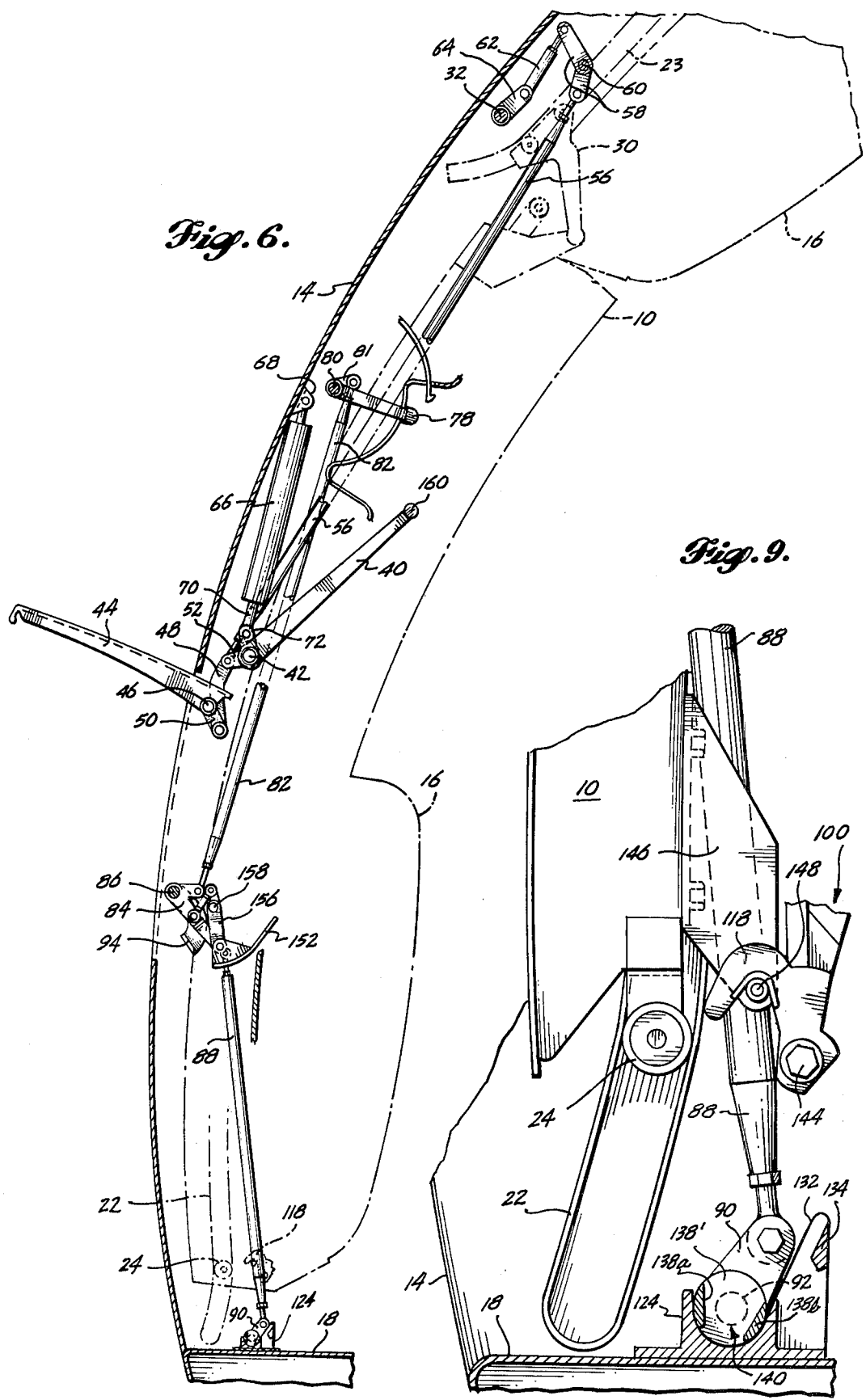

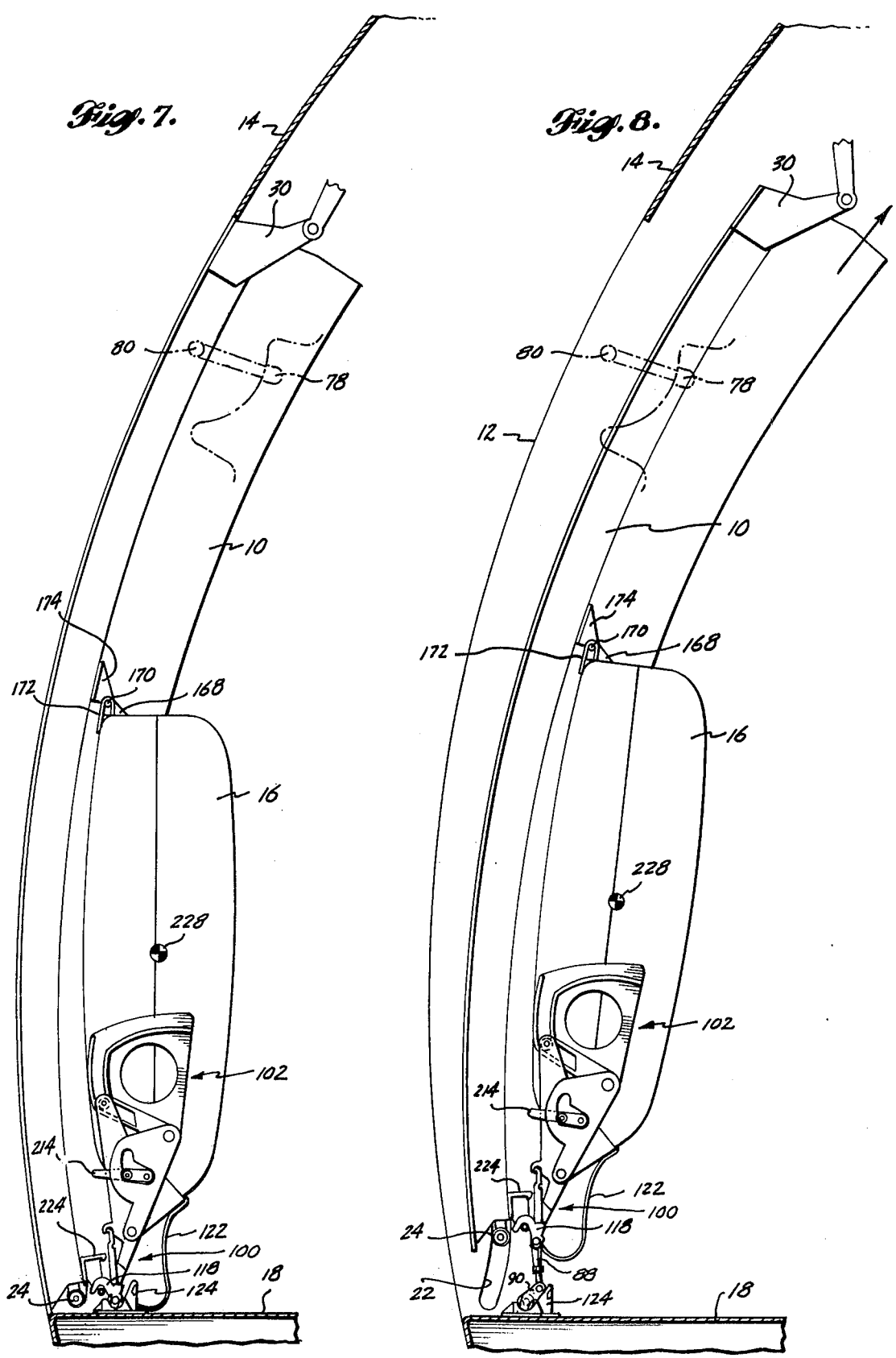

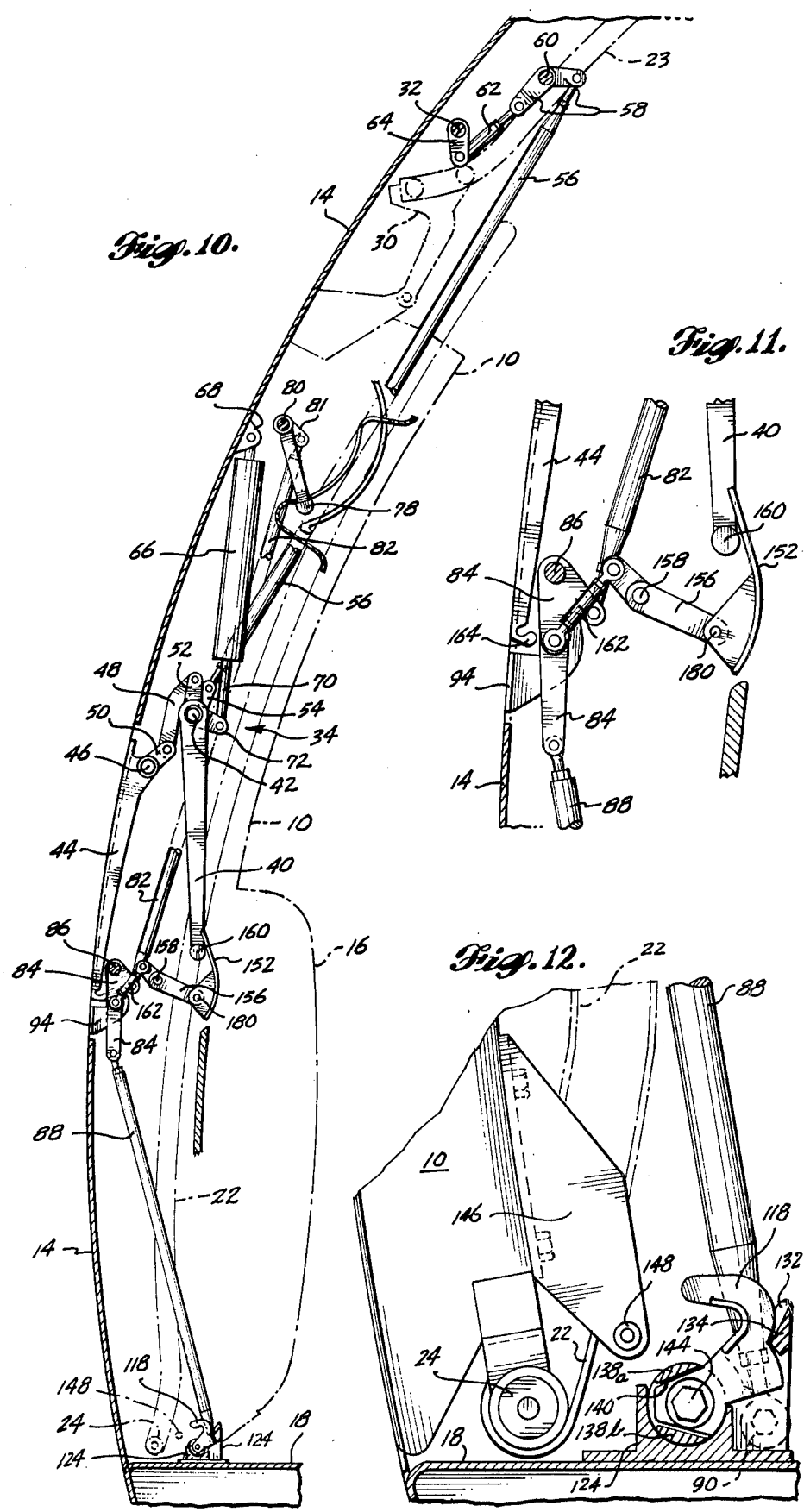

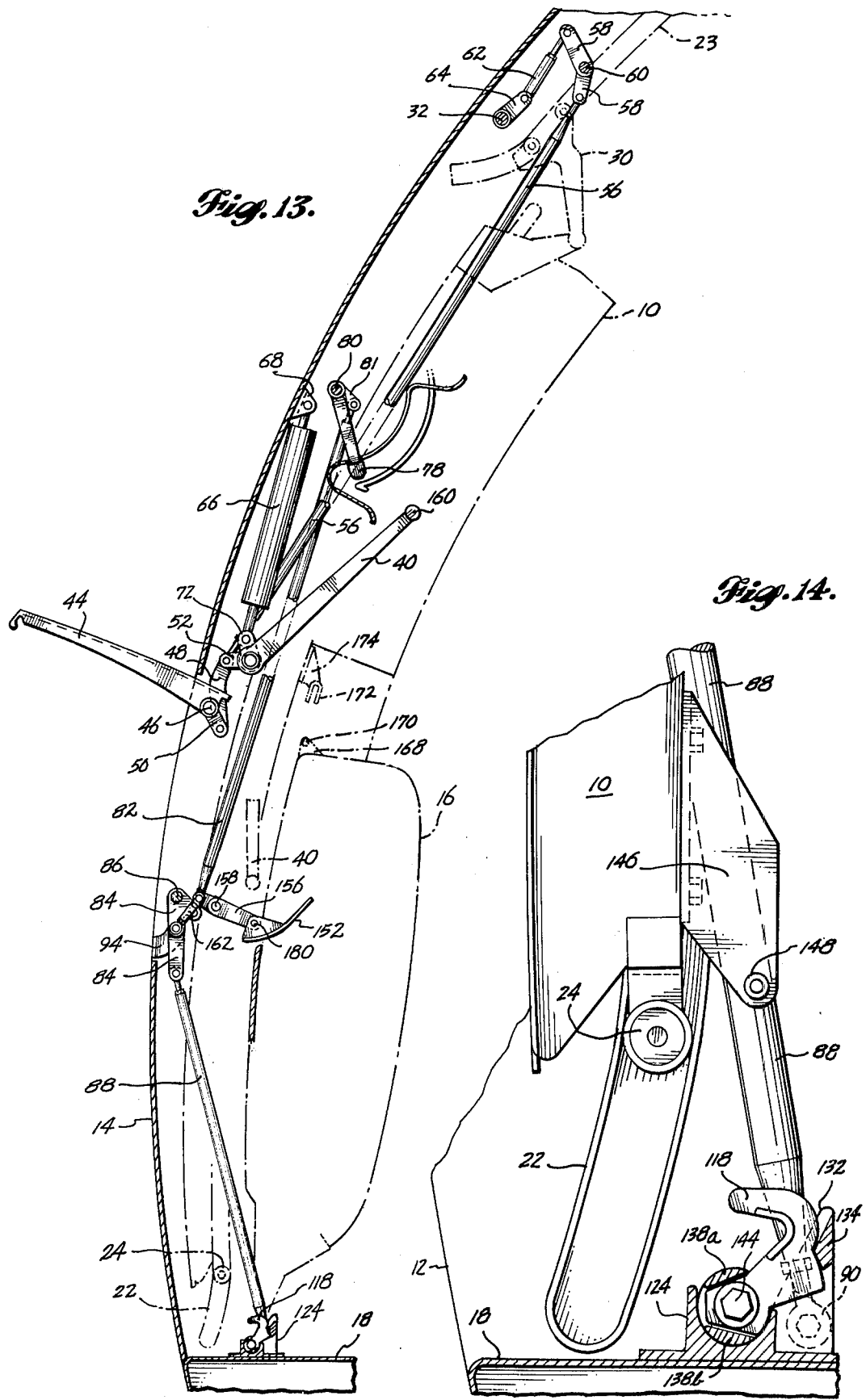

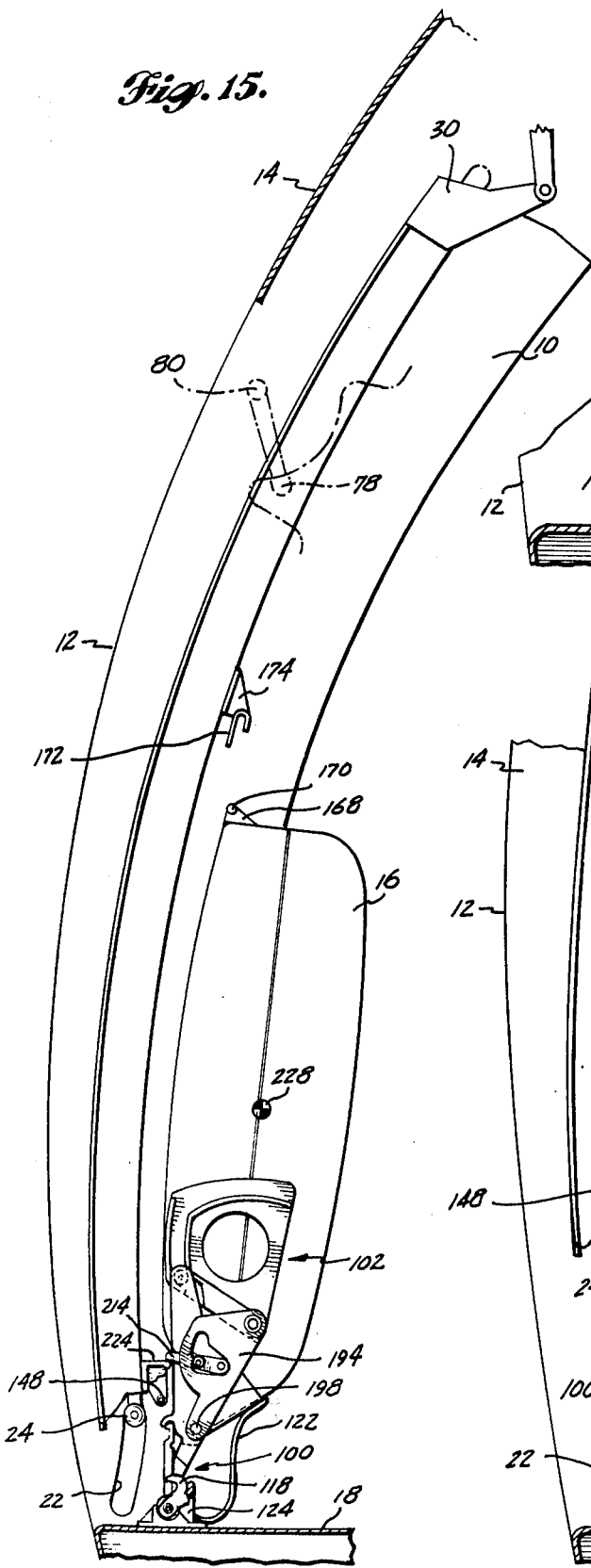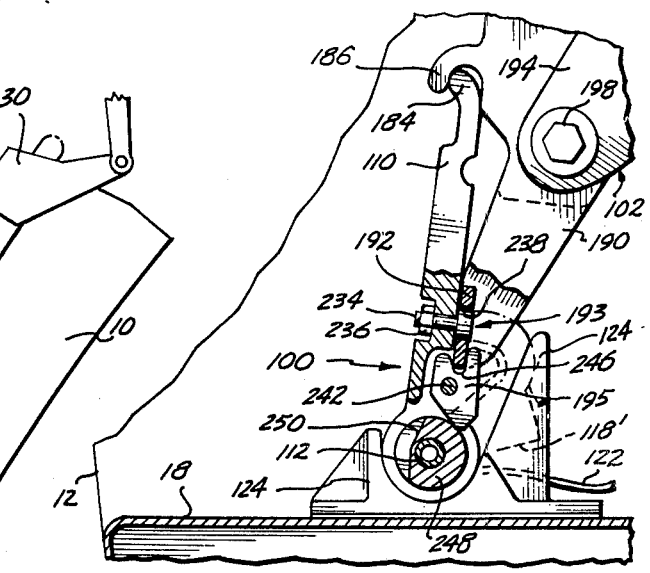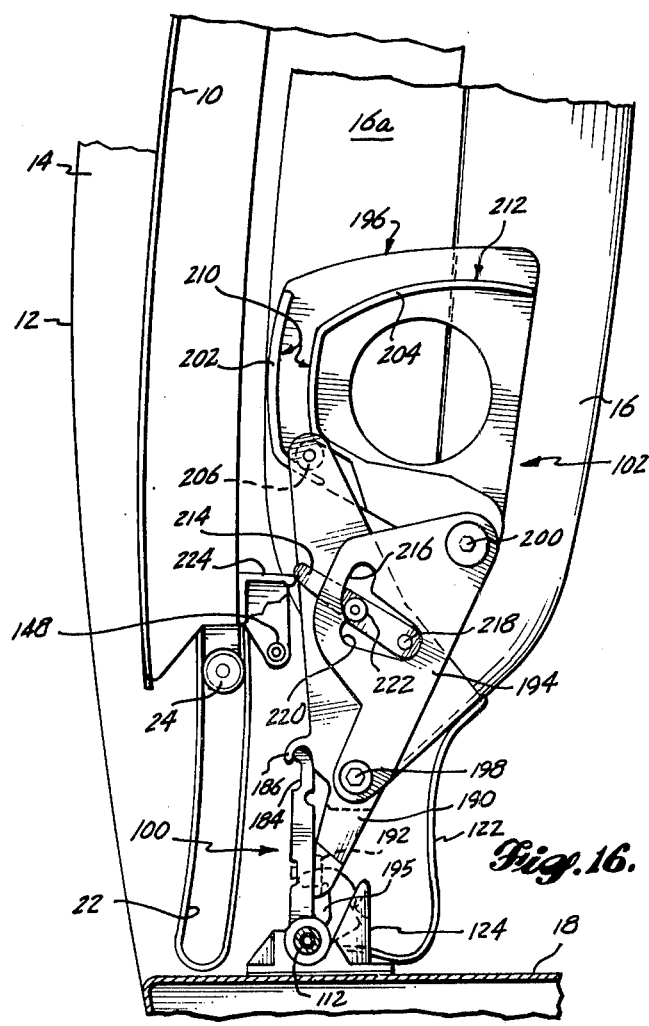

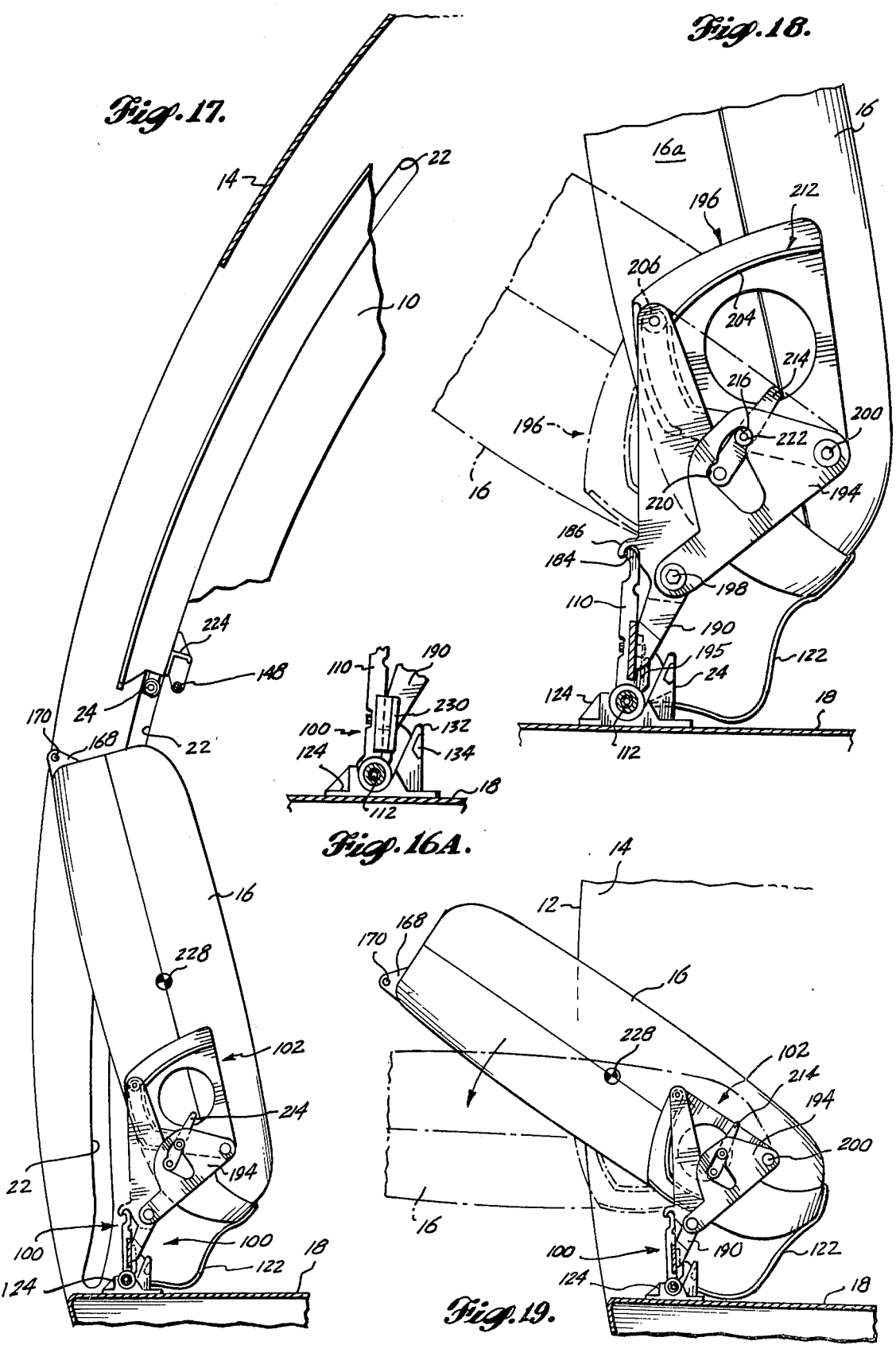

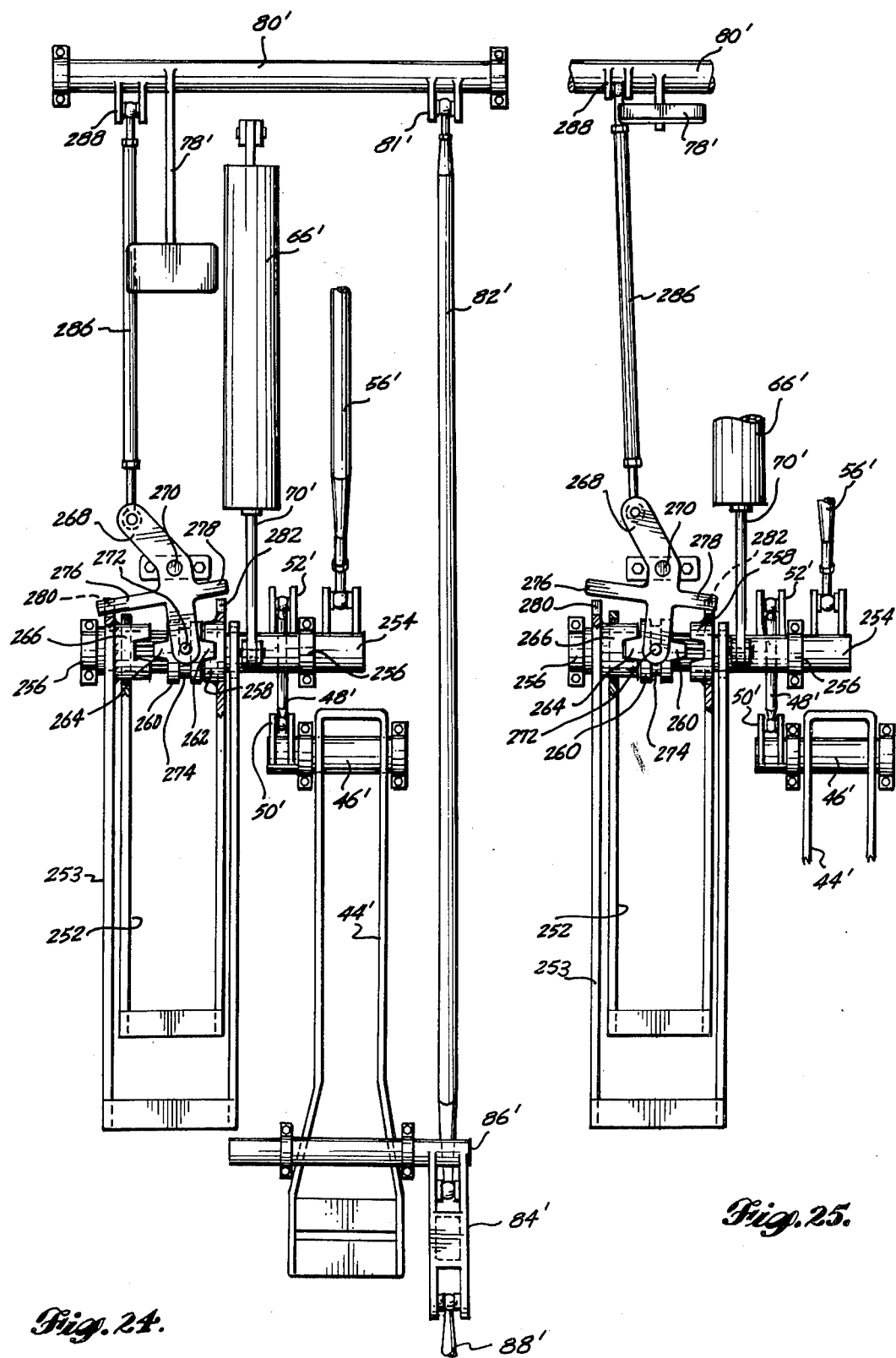

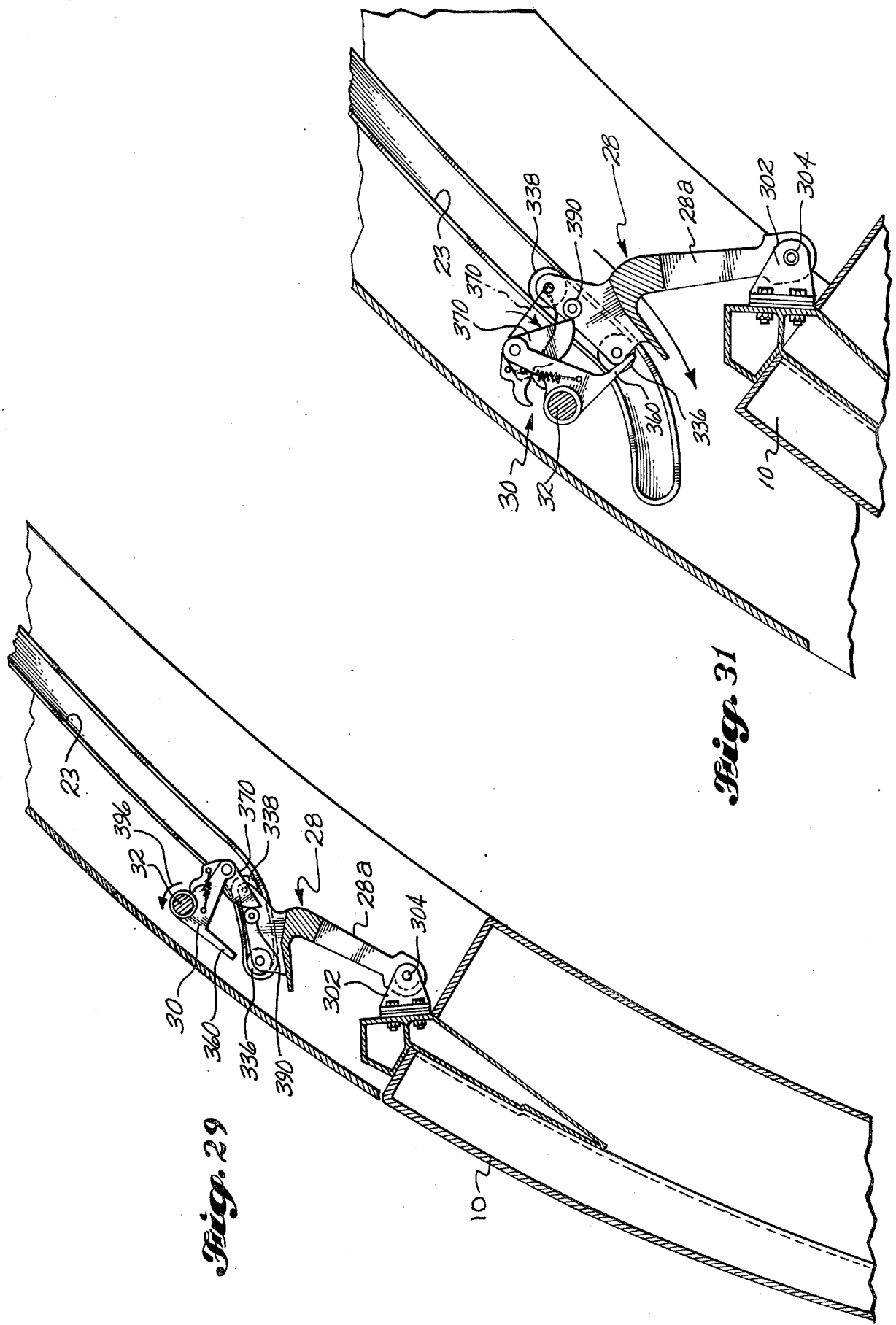

APPARATUS FOR OPENING AN AIRCRAFT DOOR AND FOR ARMING AND DISARMING AN ESCAPE SLIDE DEPLOYING MECHANISM

BACKGROUND OF THE INVENTION

The present invention relates to plug-type aircraft doors, and more particularly to actuating mechanism for unlatching, unplugging and opening an aircraft door, for closing, plugging and latching an aircraft door, and for arming and disarming an escape slide deploying mechanism used in conjunction with the aircraft door.

Commercial passenger airplanes are required to carry emergency evacuation equipment. Large commercial airplanes carry emergency evacuation or escape slides that are associated with one or more of the ingress and egress openings in the fuselage. The evacuation slides are sometimes stored in a remote but accessible location and are attached to the passenger deck adjacent the fuselage opening in an emergency situation. Conventionally, the containers for emergency evacuation slides are attached to a fuselage door under normal circumstances and are detached from the door and attached to the passenger deck adjacent the door opening either by direct manipulation of the evacuation slide container or by a manually operated, remote actuating mechanism under emergency conditions.

It is a broad object of the present invention to provide an integrated, manually actuated mechanism for arming and disarming an emergency evacuation slide mechanism attached to an aircraft door, for plugging and unplugging a track-mounted aircraft door, and for positively locking and latching the aircraft door in a closed position. Further objects of the present invention are to provide such an actuating mechanism that cannot be inadvertently manipulated when the escape slide arming mechanism is in an armed condition; to provide such an actuating mechanism for plugging and unplugging and at the same time locking and unlocking a track-mounted, overhead sliding aircraft door with a single connection to the door mechanism; to provide such an actuating mechanism that includes a positive latch to secure the door in place when it is closed in addition to the plugging and locking mechanism; to provide such an actuating mechanism that can be manipulated from inside and outside the aircraft fuselage; and to provide such an actuating mechanism that prevents the door from being opened from the outside of the fuselage when the escape slide arming mechanism is in an armed condition.

SUMMARY OF THE INVENTION

In accordance with the foregoing objects, and other objects that will become apparent to one of ordinary skill after reading the following specification, the present invention in one aspect provides an improved actuating mechanism for closing and opening and for arming and disarming a coupling means that releases an escape slide container from an aircraft door and attaches the container to the floor of the aircraft for deployment through the door opening in an aircraft fuselage. The improved acuating mechanism includes first and second interior handles mounted inside the fuselage and first and second exterior handles mounted on and accessible from the outside the fuselage. The first interior handle is mounted for swinging movement between first and second positions and is operably associated with a door opening and closing mechanism for respectively opening and closing the door upon movement of the handle between its two positions. The second interior handle is mounted on the fuselage for swinging movement between first and second positions for respectively arming and disarming the coupling means. The first exterior handle is also mounted on the fuselage for swinging movement between first and second positions and includes means for coupling it to the first interior handle so that the first interior and exterior handles are simultaneously moved between their respective first and second positions. The second exterior handle, also mounted on the fuselage for swinging movement between first and second positions, includes means for coupling it with the second interior handle to simultaneously move the second handles between their respective first and second positions. Preferably, the actuating mechanism just described includes a guard means associated with the first interior handle and mounted on the fuselage for swinging movement toward and away from a position blocking manual access to the first handle. The guard means includes a means for coupling the guard means to the second interior handle for movement to the blocking position when the second interior handle is in its first position, thereby warning an operator that the coupling means is in an armed condition to prevent inadvertent deployment of the escape slide. The first and second exterior handles are preferably mounted flush with the exterior surface of the fuselage when the exterior handles are in their respective first positions. The second exterior handle is constructed and mounted relative to the first handle so that the second handle prevents grasping of the first handle until the second handle is moved from its first to its second position to disarm the escape slide coupling means.

Another aspect of the present invention provides an improved apparatus for suspending the upper end of an track-mounted, overhead sliding door and for plugging and unplugging the door from the door opening. The improved door suspension apparatus includes an upper track means mounted on the fuselage above the door opening. The upper track means extends upwardly from a first location adjacent the upper portion of the door and a second location spaced upwardly from the first location. The upper track means has a terminal portion that curves outwardly relative to the fuselage from the first location. A carrier has followers that are operably associated with and guided by the upper track means. The carrier also has an arm that extends downwardly from the carrier and is pivotally attached at its lower end to the upper portion of the door. A rotatable member is mounted for rotation on the fuselage about an axis spaced from and oriented transversely to the upper track means. The rotatable member and the carrier include a first means for releasably coupling the rotatable member to the carrier and for transiting the carrier from a rest position in the terminal portion of the upper track means toward the upwardly extending portion of the upper track means. Preferably, a first, manually actuatable handle means, mounted for swinging movement on the fuselage between first and second positions, is coupled by a linkage means to the rotatable member. Upon actuation of the handle means, the rotatable member is caused to move via the linkage means between its first and second positions. When the rotatable member is in the first position, it is so constructed as to lock the carrier in the terminal portion of the upper track means.

When the rotatable member is moved from the first to the second position, it is so constructed and associated with the carrier as to cause the carrier to transit from the terminal portion of the upper track means toward the upwardly extending portion of the track means at the same time to release the carrier so that it can travel along the upwardly extending portion of the track means, allowing the door to move overhead of the door opening in the fuselage.

BRIEF DESCRIPTION OF THE DRAWINGS

A better understanding of the present invention can be derived by reading the ensuing specification in conjunction with the accompanying drawings wherein:

FIG. 2 is an enlarged view of the lower portion of the door, the container and the deployment mechanism shown in FIG. 1;

FIG. 2e is an elevation view of the right-hand, floor mounted support means;

FIG. 3 is a simplified cross-sectional view taken substantially along section line 3—3 of the actuating mechanism for locking and unlocking the door and for deploying the slide, showing a latch hook but omitting the remainder of the deployment mechanism, showing the door and the slide container in phantom outline, and showing the actuating mechanism in the disarmed mode;

FIG. 4 is a greatly enlarged view of a segment of FIG. 3 showing the door and latch hook for connecting the deployment mechanism and slide container to the door in the disarmed mode;

FIG. 5 is an enlarged view of the hand-manipulated portion of the door opening mechanism as shown in FIG. 3;

FIG. 6 is a view similar to FIG. 3 showing the actuating mechanism in the disarmed mode and unlocked position with the door partially opened and the slide container attached to the door;

FIG. 7 is a simplified cross-sectional view of the over-center linkage forming part of the deployment mechanism with the door closed and the container attached to the door, corresponding to the position of the actuating mechanism in the unarmed mode as illustrated in FIG. 3;

FIG. 8 is a view similar to FIG. 7 showing the door partially opened with the container attached to the door, corresponding to the position of the actuating mechanism in the unarmed mode as illustrated in FIG. 6;

FIG. 9 is a greatly enlarged view of a portion of FIG. 8 showing the latch mechanism with the door partially opened and with the over-center linkage deleted for clarity;

FIG. 10 is a simplified cross-sectional view similar to FIG. 3 showing the actuating mechanism in the armed mode with the door closed;

FIG. 11 is a greatly enlarged view similar to FIG. 5 of the hand manipulated portion of the door opening mechanism showing the safety shield over the interior door opening handle, and corresponding to the position of the actuating mechanism in the armed mode as illustrated in FIG. 10;

FIG. 12 is a greatly enlarged view of the latch hook similar to FIG. 4 but showing the hook attached to the floor and released from the door, and corresponding to the position of the actuating mechanism in the armed mode as illustrated in FIG. 10;

FIG. 13 is a view similar to FIG. 10 showing the actuating mechanism in the armed mode and unlocked position with the door partially opened and the container attached to the floor;

FIG. 14 is a greatly enlarged view similar to FIG. 12 but showing the door partially raised and the latch hook attached to the floor, and corresponding to the position of the actuating mechanism in the armed mode as illustrated in FIG. 13;

FIG. 15 is a simplified view of the door, container and over-center linkage similar to FIG. 8 showing the door partially raised with the container attached to the floor, and corresponding to the position of the actuating mechanism in the armed mode as illustrated in FIG. 13;

FIG. 16 is a greatly enlarged view of the door, container and over-center linkage as illustrated in FIG. 15;

FIG. 16a is an enlarged view in partial section of a portion of FIG. 16 showing the stop flange on the girt bar assembly omitted in the preceding side views for simplicity in illustration;

FIG. 17 is a view similar to FIG. 15 showing the container and over-center linkage in the armed mode after the door has risen above the container and immediately after the center of gravity of the container has been shifted;

FIG. 18 is an enlarged view of the over-center linkage shown in FIG. 17;

FIG. 19 is a view similar to FIG. 17 showing the container rotating downwardly and outwardly about the over-center linkage;

FIG. 21 is a greatly enlarged cross-sectional view taken substantially along section line 21—21 of FIG. 2a showing the girt bar separation mechanism for separating the container from the floor and corresponding to the position of the over-center linkage as illustrated in FIG. 16;

FIGS. 24 and 25 are enlarged views of an alternate embodiment of the actuating mechanism for opening and closing the door and for the arming and disarming the container deployment mechanism, showing the actuating mechanism in the locked position and, respectively, in the armed and disarmed modes, respectively;

FIG. 27A is a partial sectional view taken along section lines 27A—27A of FIG. 27;

FIG. 29 is a side view of the upper portion of the door showing the carrier and the plugging and unplugging mechanism in the locked position;

FIG. 30 is a view similar to FIG. 29 showing the plugging and unplugging mechanism after the carrier and thus the door are moved to an unplugged position; and FIG. 31 is a view similar to FIGS. 29 and 30 showing the carrier on its return toward the terminal portion of the upper track and showing the plugging arm on the carrier in its partially tripped position.

DETAILED DESCRIPTION

Figure 1:
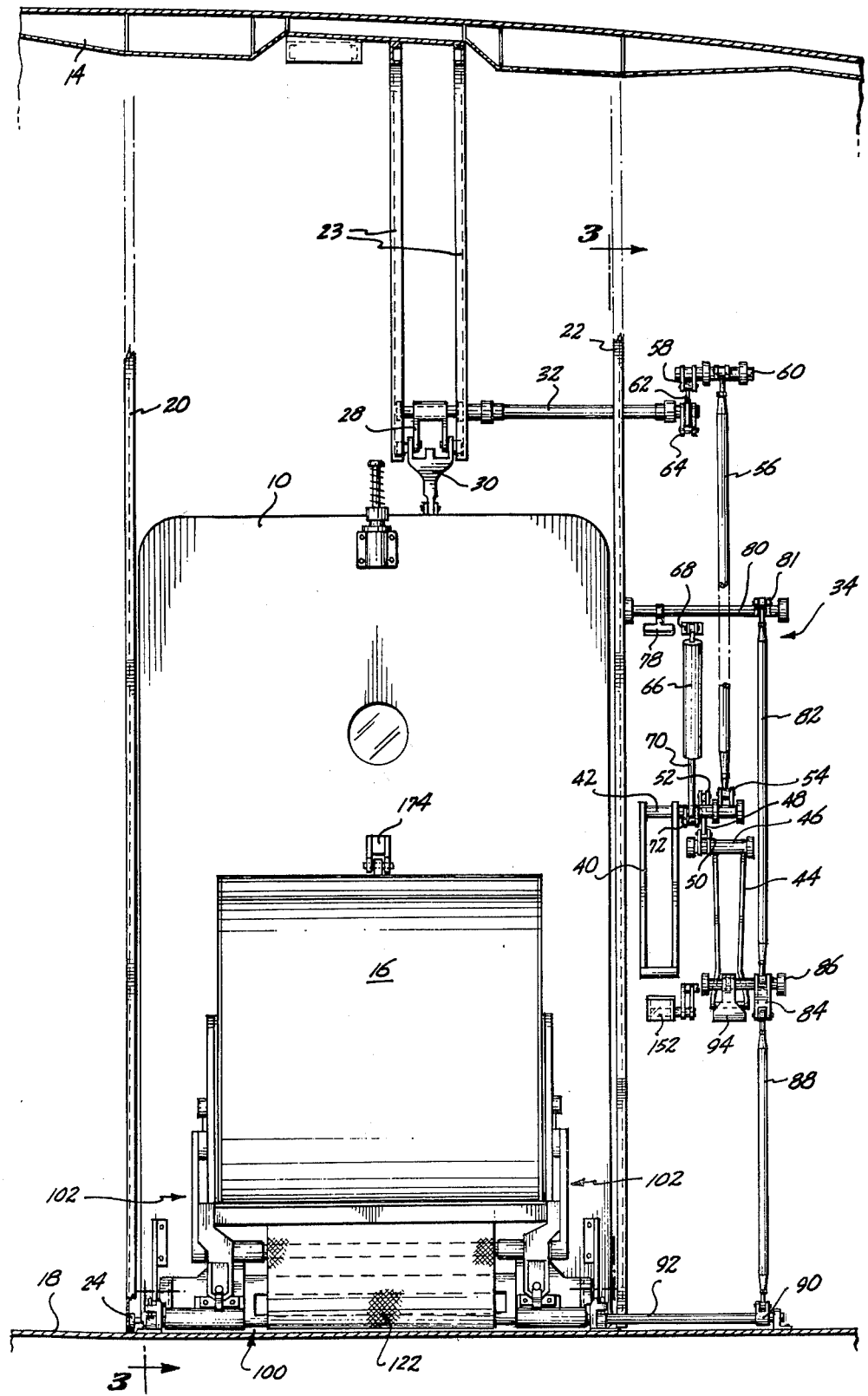
FIG. 1 is a view of a segment of an aircraft fuselage, an overhead, track-mounted, sliding door in a closed position, an escape slide container and associated mechanism attached to the door, and the slide deployment, actuating and door opening mechanism, in partial cross-section looking outwardly from inside the fuselage.

Referring first to FIGS. 1 and 3, an overhead, track-mounted door 10 is positioned in a door opening 12 in the fuselage 14 of an aircraft. An emergency escape slide (or chute) container 16 is mounted on the inside of the door 10 and normally rises upwardly with the door as the door is raised. Under emergency conditions, the door can be raised while the slide container 16 is released from the door and attached to the passenger deck 18 in the fuselage 14 in readiness for deployment of the escape slide. The door, although very simply depicted, is of the plug type that seals against periphery of the the door opening in the fuselage to maintain a desired internal cabin pressure. The door 10 is mounted in left and right tracks 20 and 22 and an overhead track 23 comprising two guideways. Track followers 24 and 26 mounted at the lower corners of the door engage, respectively, the left and right tracks 20 and 22. An overhead truck or carrier 28, which rides in the overhead track 23, is pivotally attached to the upper edge of the door. The overhead sliding door can be counterbalanced for manual raising and lowering or can be powered in its upward and downward opening and closing traverse of the tracks 20, 22 and 23 by an electric motor or other prime mover. The truck 28 is coupled by a locking and unlocking mechanism 30 to a locking and unlocking shaft 32, which is journalled above the door to a structural portion of the fuselage (not shown) and extends sidewardly from the door beyond the right track 22. The locking and unlocking shaft 32 is mechanically coupled to the manually operated, door opening and closing (or unlocking and locking) mechanism and manually operated, deployment arming and disarming mechanism, generally designated 34.

The manually operated door opening and arming mechanism 34 for deployment of the slide container will first be described in conjunction with FIGS. 1, 3 and 10. The arming mechanism is illustrated in FIGS. 1 and 3 in a disarmed mode ready for opening the door without deploying the escape slide. When the door is in its normally closed position, for example during normal flight conditions (as shown in FIG. 10), the arming mechanism is in its armed mode ready for deployment of the slide by merely opening the door. First, however, the normal operation of the door will be described in conjunction with first disarming the mechanism and thereafter opening the door so that the escape pack will remain attached to the door and rise with the door as it traverses overhead of the door opening 12.

The door opening and closing mechanism includes an interior handle 40 affixed to a horizontally oriented shaft 42, which is parallel to the fuselage and journalled on internal fuselage structure (not shown). An exterior handle 44 is affixed to a horizontally oriented shaft 46, which is parallel to the fuselage and journalled for rotation on internal fuselage structure (not shown). A link 48 interconnects the interior and outside handles for simultaneous movement between a closed and latched position as shown in FIGS. 1, 3 and 10, and an unlocking position (described below in conjunction with FIG. 6). The lower end of link 48 is connected to an upwardly extending arm 50 affixed to the exterior handle mounting shaft 46 while the upper end of the link 48 is pivotally coupled to an upwardly extending arm 52 affixed to the interior handle mounting shaft 42. A second arm 54 is affixed to and extends upwardly from the interior handle mounting shaft 42 and is pivotally coupled to a long, upwardly extending link 56. The upper end of link 56 is pivotally coupled to a bell crank-like member 58 affixed to shaft 60, which in turn is mounted for rotation about a horizontal axis on internal fuselage structure (not shown). The other end of the bell crank-like member 58 is pivotally connected to a link 62 in turn connected to a downwardly extending arm 64 affixed to the locking and unlocking shaft 32. The upper end of an over-center, spring 66 (a conventional compression spring cartridge) is pivotally connected to a bracket 68 affixed to the fuselage. The piston rod 70 of the spring is pivotally connected to an inwardly extending arm 72 affixed to the interior handle mounting shaft 42. The spring 66 retains the locking and unlocking handles 40 and 44 in their latched positions via a restraining force on the arm 72.

The actuating handle for arming and disarming the escape slide pack extends inwardly (in FIGS. 1 and 3) from a horizontally oriented, arming handle shaft 80 in turn journalled to internal fuselage structure (not shown) for rotation about an axis parallel to the fuselage. An upwardly and inwardly extending arm 81 affixed to the arming handle shaft 80 is pivotally coupled to a connecting link 82 that extends downwardly to adjacent the location of the interior and exterior handle mounting shafts. The other end of the connecting link 82 is pivotally coupled to the inwardly extending, short arm of a bell crank 84 affixed to a horizontally oriented shaft 86, in turn mounted on internal fuselage structure (not shown). The long arm of bell crank 84 extends downwardly and inwardly from the shaft 86 and is pivotally coupled to a second connecting link 88 in turn extending downwardly to a location adjacent the passenger deck 18. The bottom end of the connecting link 88 is pivotally coupled to an arm 90 extending inwardly and upwardly from arming and disarming torque tube 92. The torque tube 92, which extends horizontally along the passenger deck to a location adjacent the bottom right-hand corner of the door 10, operates, by means to be described in more detail below, the mechanism for selectively connecting the pack to the door for upward traverse therewith under normal circumstances, or connecting the escape slide container 16 to the floor in readiness for deployment through the door opening.

An exterior disarming handle 94 is also affixed to the shaft 86 and is thereby mounted for simultaneous movement with the interior arming handle 78. The hand grip portion of the exterior disarming handle 94 is located adjacent the bottom of the exterior door opening handle 44 so that the exterior door opening handle cannot be grasped until the exterior disarming handle is moved to its disarmed position as shown in FIGS. 1 and 3.

Figure 2A:
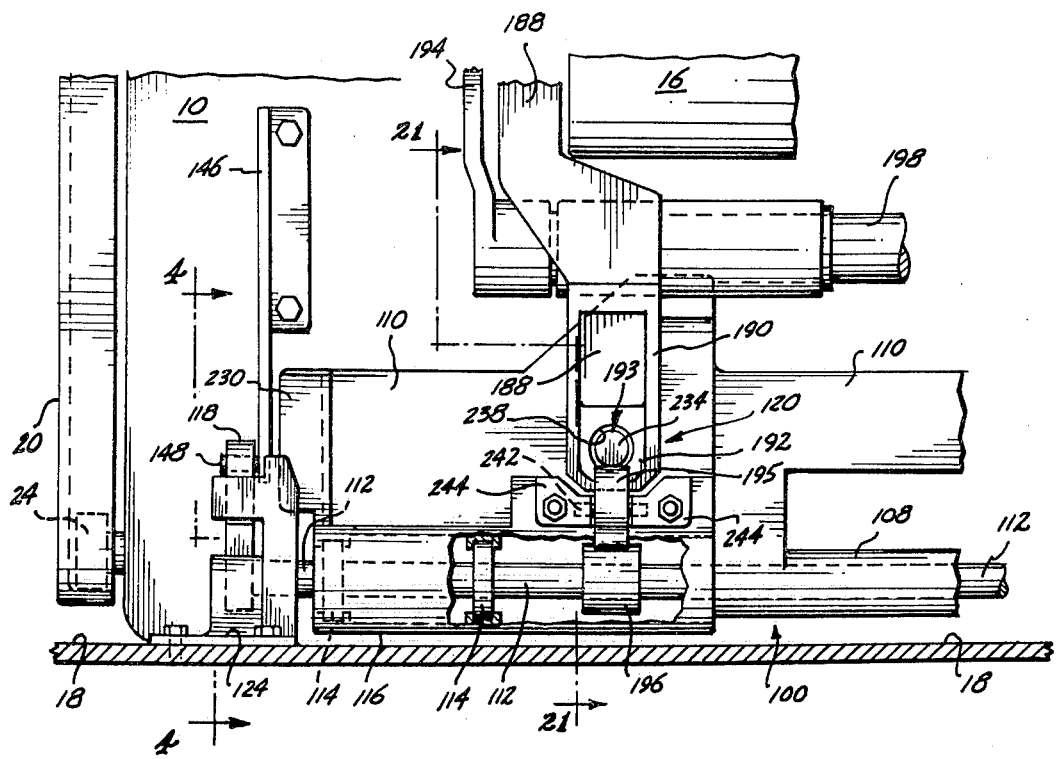
FIG. 2a is a greatly enlarged view of the lower, left-hand portion of the door, deployment mechanism, and container illustrated in FIG. 2.

Before discussing the operation of the door opening and disarming handles and the associated mechanism, a better understanding of construction of the girt bar assembly, generally designated 100, is necessary. The girt bar assembly attaches the slide container 16 to the passenger deck 18 when the actuating mechanism is in an armed mode for deployment of the container. The container is normally supported above the girt bar assembly 100 by an over-center linkage, generally designated 102, which functions as a part of the deployment mechanism for the escape slide. Referring to FIGS. 2 and 2a, the girt bar assembly comprises a tubular lower portion 108 and a normally upwardly oriented plate member 110 extending substantially the length of the tubular portion 108. A torque tube 112 extends through and beyond the tubular portion 108 of the girt bar and is journalled in bearings 114 mounted in bosses 116 located at opposite ends of the tubular portion 108 of the girt bar. The torque tube extends beyond opposite ends of the girt bar assembly. Hooks 118 (also viewed in FIG. 4, which omits the over-center linkage and all of the girt bar assembly except the torque tube and the hook) are attached to each end of the torque tube 112. The over-center linkage 102 is in turn detachably connected by latch fittings 120 to the plate member 110 of the girt bar assembly and normally supports the slide container 16 above the girt bar. A girt strap 122 is affixed to the plate portion 110 of the girt bar assembly 100 (by means not shown) and extends upwardly therefrom and is also affixed through the bottom end of the slide container 16 to the chute or slide packed within the container. The girt strap 122 is composed of a flexible fabric material that constitutes a flexible coupling between the tubular portion 108 of the girt bar assembly and the slide container once it is detached from the girt bar after deployment.

Figure 2B:
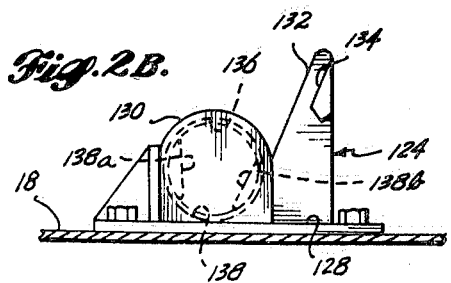
FIGS. 2b, 2c and 2e are end, top and side elevation views, respectively, of the left-hand floor mounted support means forming part of the deployment mechanism.
Figure 2D:
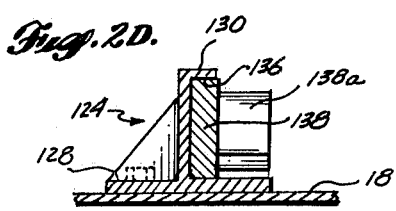
FIG. 2d is a sectional view taken along section line 2d—2d of FIG. 2c.
Figure 2C:
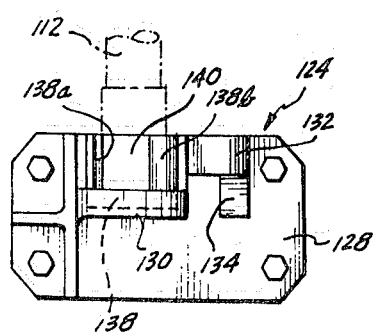
Figure 2E:
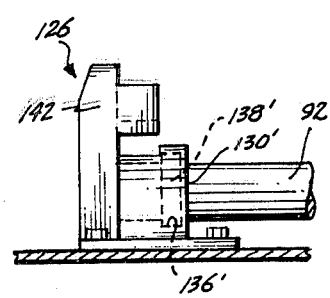

The outer ends of the girt bar torque tube 112 and the hooks 118 rest in floor fittings 124 (also seen in FIG. 4) positioned adjacent the bottom and sides of the door 10 and affixed by conventional means to the passenger deck floor 18. The floor fitting 124 on the left-hand side of the door is best illustrated in FIGS. 2b, 2c and 2d while the right-hand floor fitting 126 is best illustrated in FIG. 2e. Referring to FIGS. 2b through 2d, the left-hand floor fitting has a base member 128, a journal 130, an upright girt bar stop 132 and a hook stop 134 that extends transversely from the upper portion of the girt bar stop 132 in a direction perpendicular to the plane of rotation of the girt bar torque tube 112 and the hook 118. A horizontal bore 136 having an axis oriented parallel to the girt bar torque tube 112 is provided in the journal 130 and opens to the right toward the girt bar assembly in a circularly shaped opening. The upper portion of the journal adjacent the door opening is removed, leaving an upwardly opening U-shaped trough 136a in the journal. The trough forms an extension of the bore 136 in the portion of the journal adjacent the location of the end of the girt bar torque tube 112 and the hook 118. A rotatable latch member 138 has one end rotatably mounted in the bore 136 and has two, spaced, axially extending arms 138a and 138b that extend into the trough 136a and define a downwardly convergent slot 140 through the latch member. The outer circumferential surfaces of the arms 138a and 138b conform to the circumferential curvature of the trough 136a while the inner surfaces of the arms are flat and inclined relative to each other to form a downwardly convergent, trapezoidally shaped slot 140.

The right-hand floor fitting 126 is constructed similarly to the left-hand floor fitting 124 just described except that it consistutes the mirror immage of the left-hand floor fitting, and, further, the bore 136' in the right-hand fitting 126 extends completely through the journal 130'. The end of the rotatable latch member 138' journalled in the bore 136' situated on the opposite side of the right-hand fitting 126 from the girt bar assembly 100 is affixed to the disarming torque tube 92 in turn coupled to the manually operated, arming and disarming mechanism.

As shown in FIGS. 2a and 4, the bottom portion of the hook 118 is trapezoidally shaped at its connection to the girt bar torque tube 112 and is secured to the torque tube 112 by a suitable fastener 144. When the door is in its closed position, the bottom portion of the hook 118 fits into the trapezoidally-shaped slot 140 formed by the arms 138a and 138b of the rotatable latch member 138. The rotating latch member is constructed and rotated to a position such that when the arming and disarming mechanism is in its disarmed mode, the hooks 118 can be lifted out of the rotatable latch member 138. The right-hand latch member 138, and the right-hand hook 118 are similar in construction and function to the corresponding left-hand components. Whenever reference is made to the left-hand components below, it will be understood by one of ordinary skill that the right-hand components are the same, with the exception that the right-hand components are generally constructed as the mirror image of those on the left-hand side. If the right-hand components differ signficantly, they will be mentioned and specifically described.

Brackets 146 and 146' affixed to the bottom portion of the door adjacent the locations of the hooks 118 and 118', have transversely extending lift pins 148 and 148' affixed thereto. Referring to FIGS. 2a and 4, the left-hand hook 118 fits over the lift pin 148 when the assembly is in the disarmed mode so that when the door is raised, the hook member, and thus the girt bar assembly 100, the over-center linkage 102 and the slide container 16, are lifted out of the rotatable latch member 138 and carried upwardly by the door to an overhead, out of the way location so that normal passenger ingress and egress can be effected through the door opening.

Referring again to FIG. 10, the actuating mechanism for opening the door and for arming the escape slide deployment mechanism is shown in the normally closed position in the armed mode. In this position and mode, the arming handle 78 is in a downwardly and inwardly extending position, which shifts the connecting link 88 downwardly, in turn positioning the bell crank 84 so that the connecting link 88 rotates the girt bar torque tube 112 and thus the hook 118 to the armed position, (that is, disengaged from the supporting pin 148 affixed to the door bracket 146 as shown in FIGS. 10 and 12). Before the door is opened under normal (non-emergency) conditions, the arming handle 78 is rotated counterclockwise so as to rotate its mounting shaft and thus arm 81 to raise the connecting link 82 as shown in FIG. 3. As the upper connecting link 82 of the arming mechanism is raised, the bell crank 84 is rotated in a counterclockwise direction to lift lower connecting link 88 and thus rotate the girt bar torque tube 112 in a counterclockwise direction, positioning the hooks 118 and 118' over the lift pins 148 and 148' on the door (as shown in FIGS. 3 and 4). The hooks 118 and 118' are spaced above the pins 148 and 148' when the door is closed and the container is resting in the floor fittings to allow the hooks to be easily engaged and disengaged from the pins.

Referring to FIGS. 3, 5, 10 and 11, when the arming mechanism is in the armed mode, a safety shield 152 is positioned in front of the interior door opening handle 40. The safety shield 152 is pivotally mounted on a bell crank 156, which is in turn journalled on a shaft 158 mounted on fuselage structure (not shown) inboard from and substantially parallel to and adjacent the bell crank shaft 86. The bell crank 156 is coupled by a link 162 interconnecting one arm of the safety shield bell crank 156 to the arming bell crank 84. As the arming bell crank is rotated to a disarmed position in reaction to movement of the arming handle 78, the shield bell crank 156 is rotated in a clockwise direction about the shaft 158 to remove the shield from its position in front of the hand grip 160 of the interior door opening handle 40 (as shown in FIG. 12) to a position clearing the hand grip for use (as shown in FIG. 5). At the same time, the exterior disarming handle 94, affixed to the arming bell crank 84, is rotated inboard in a counterclockwise direction. The exterior disarming handle 94 is so positioned in its normally armed position (FIG. 11) as to prevent access to the hand grip portion 164 of the exterior door opening handle 44. However, when the arming mechanism is in a disarmed mode (FIGS. 3 and 5), the hand grip portion 164 of the exterior door opening handle 44 can be grasped from the outside. Also, if the door is opened from the outside, inward movement of the exterior disarming handle 94 will serve to rotate the arming bell crank 84 in a counterclockwise direction to place the arming mechanism in a disarmed mode.

The door opening mechanism shown in FIG. 3 is now in its ready position for unlocking and raising the door 10 from the door opening 12. The door is unlocked by grasping the hand grip 160 on the interior door opening handle 40, or by grasping the hand grip 164 on the exterior handle 44, and by swinging the handles upwardly about their respective mounting shafts 42 and 46. As one or the other of the handles 40 and 44 is swung upwardly to the position shown in FIG. 6, the door unlocking link 56 attached to arm 52 on the interior handle mounting shaft 42 is pulled downwardly. The motion of the unlocking link 56, through the bell crank-like member 58, link 62 and arm 64 rotates the unlocking shaft 32 to pull the truck 28 inwardly along the upper central track 24, thus unplugging the door from the door opening 12 and causing it to begin its upward and overhead traverse along the mounting tracks 23, 20, and 22. The door 10 can then be raised to the overhead position shown in double-dashed phantom outline at the upper portion of FIG. 6, thus clearing the door opening 12 for normal ingress and egress.

When closing the door under normal circumstances, the door is lowered from its overhead position toward its plugged position. After it is adjacent its plugged position, either the interior or exterior opening handle 40 or 44 is rotated downwardly to the position shown in FIG. 10 and thereafter the arming handle 78 is rotated downwardly to the position shown in FIG. 10 to arm the escape slide deployment mechanism and to rotate the exterior disarming handle 94 to its position below the exterior opening handle 44 and flush with the outer skin of the fuselage.

Still referring to the normal opening sequence of the door, reference is made to FIG. 7 wherein the escape slide container 16 and associated mechanism is shown attached to the door, the arming mechanism is shown in the disarmed mode, and the door is shown in a closed position. The hook 118 is positioned over the lift pin 148 on the bracket 146 affixed to the door 10 and the rotatable latch member 138 is positioned so that the hook member and thus the girt bar assembly 100, the over-center linkage 102 and the container 16 can move upwardly with the door. The container 16 in this position is secured at its upper end by a secondary latch associated with the upper end of the container and the door. A latch flange 168 is affixed to and extends upwardly from the upper, central, outboard portion of the container. A horizontally oriented pin 170 is affixed to the flange and spaced above the upper end of the container and engages a downwardly opening, U-shaped latch member 172, affixed to a flange 174 projecting inwardly from the inboard side of the door. When the door is closed and the container is resting on the floor fittings 124, the U-shaped latch member 172 is positioned over the pin 170, thus cooperating to prevent the container from falling inboard as the door 10 is unplugged from the door opening 12 and begins its overhead traverse along the tracks.

Referring now to FIGS. 8 and 9, the door is illustrated in a partially raised position. The girt bar assembly 100, over-center linkage 102, and the slide container all rest on the hook 118 and are carried upwardly by the door as it begins its overhead traverse. The upper portion of the container is secured to the door since there is no change in the vertical relationship between the upper latch pin 170 and the latch member 172 on the door.

Referring now to FIGS. 1, 2a, 10, 11, and 12, the deployment mechanism is in its armed mode. As previously stated, the deployment mechanism is armed when the door is normally closed during flight. In this position, the safety shield 152, shown in enlarged scale in FIG. 11, is positioned in front of the hand grip 160 on the interior handle 40. The safety shield 152 is rotatably mounted on the inwardly extending arm of bell crank 156 by pin 180. A torsionally wound coil spring (not shown) rotationally biases the safety shield 152 about the pin 180 to a position where the shield is located inboard and adjacent the hand grip 160 of the interior handle 40. To open the door 10 when the deployment mechanism is in the armed mode, a force is applied to the upper end of the safety shield 152 and it is rotated about pin 180 to expose the hand grip 160 of the interior unlocking and opening handle 40.

Referring to FIGS. 10 and 12, the arming handle 78 is shown rotated downwardly to its armed position. Through links 82 and 88 and bell crank 84, the arm 90 on the disarming torque tube 92 (FIG. 1) is rotated in a clockwise direction, thus rotating the girt bar torque tube 112 (FIG. 2a) in a clockwise direction. Since the door is closed and the container 16 is positioned adjacent the floor, the trapezoidal bottom portion of the latch hook 118 is seated within the slot formed by arms 138a and 138b of the rotatable latch members 138 situated in both of the floor fittings 124 and 126. It again should be understood that the entire description of the embodiment will be described in relation to the left-hand side of the assembly. The right-hand side of the deployment mechanism operates in the same manner but constitutes the mirror image of the portion of the assembly on the left-hand side of the structure. Thus, further description of the right-hand portion of the mechanism has been omitted. As the girt bar torque tube 112 is rotated in a clockwise direction, the hook 118 is also caused to rotate in a clockwise direction, disengaging the upper portion of the hook from the latch pin 148 on the door bracket 146. This rotation serves two functions: first to disengage the container 16 from the door and second to secure the girt bar assembly 100 to the floor fittings 124. It will be noted that the hook 118 is rotated so that its inboard end rests against the hook stop 134 on the floor fitting 124. The rotatable latch member 138 in the armed position cooperates with the trapezoidal bottom portion of the hook 118 to prevent removal of the hook and thus the girt bar assembly and the container from the floor fitting 124.

When it is desired to open the door 10, the safety shield 152 is rotated to clear the hand grip 160 of the interior unlocking and opening handle 40 as shown in FIG. 13. The interior handle 40 is then rotated upwardly in a counterclockwise direction so as to rotate its mounting shaft 42 in the same direction. As the handle is rotated, the door unlocking and opening linkage is operated in the same manner as explained in conjunction with FIG. 6 when the door was opened with the arming mechanism in an unarmed mode. Thus the door begins its upward traverse as shown in phantom outline in FIGS. 13 and 14. As this occurs, the container remains attached to the passenger deck 18 via the hook 118, rotatable latch member 138 and the floor fitting 124. As the door begins its upward traverse, the U-shaped latch member 172 moves upwardly with the door and frees the upper latch pin 170 affixed to the upper end of the container. The door can then continue in its upward traverse, freeing the pack from the door and clearing the door opening 12 in the fuselage 14.

As the door moves upwardly to clear the container, it serves one additional function, namely to trip the over-center linkage 102 and shift the center of gravity 182 of the container 16 so that it will deploy itself through the door opening 12 under the urging of gravity and without further manual assistance. Before explaining the means for tripping the over-center linkage 102, detailed description of the construction and arrangement of the parts of the over-center linkage will be presented.

Referring to FIGS. 2, 2a, 15 and 16, the plate portion 110 of the girt bar assembly 100 has an upwardly extending flange 184 that mates with a hook 186 positioned on the outboard side of a separable link 188. The flange 184 extends upwardly from the plate portion 110, forming part of the girt bar assembly when the container is in its normal, stable condition. A downwardly extending arm 190 on the separable link 188 has a transverse end portion 192 containing an aperture that, when assembled, mates with a protrusion 193 on the plate portion 110 of the girt bar assembly situated below the upwardly extending flange 184 on the plate portion 110. A can follower or panel 195 holds the downwardly extending end portion 192 of the separable link 188 in position so that the aperture engages the protrusion 193. Thus the cooperation of the upwardly extending flange 184 engaging the hook 186 on the separable link and the downwardly extending end portion 192 held in place on the protrusion by the cam follower 195 maintains the plate portion 110 and the separable link 188 as an integral unit prior to the time the pack assembly 16 is completely deployed. (The cam follower or panel 195 and the mechanism for releasing the follower and thus allowing the separable link 188 to separate from the plate portion 110 of the girt bar is shown in FIG. 21 and will be described in further detail below).

The separable link 188, a second link 194 that is pivotally coupled to both the separable link 188 and the container 16, and a cam member 196 mounted on the outboard half 16a of the escape slide container cooperate to form the over-center linkage 102 for deploying the safety slide container under the urging of gravity. The second link 194 has its lower end pivotally attached by shaft 198 to the separable link 188 at a location inboard from the position of the hook 186 on the separable link. The shaft 198 extends under the escape slide container and couples with the corresponding second link on the right-hand side of the pack, thereby coupling the second link 194 to the right-hand separable link. The upper end of the second link 194 is pivotally coupled by shaft 200 to an inboard extension of the cam member 196.

The cam member 196 has a double sided cam surface formed by two sidewardly extending, equally spaced flanges 202 and 204. The mutually opposing surfaces of the flanges 202 and 204 form the cam structure in which a follower 206, mounted on the upper end of the separable link 188 for rotation about an axis parallel to the axis of shaft 198, is positioned. The shape of the cam surface formed by the flanges 202 and 204 will be explained as they are oriented relative to the vertical extent of the container when it is positioned in its upright, undeployed location. The cam surface has a lower portion that extends outwardly and slightly upwardly from an inboard location. The lower portion is joined by a slightly outwardly concave, but generally vertically oriented cam portion 210. The outboard one of the two flanges 202 and 204 terminates at the upper end of the vertical cam portion 210 while the inboard flange 204 joins with the cam portion 210 and extends inboard to form a third cam portion 212. When the pack is in its undeployed position, the follower 206 mounted on the upper end of the separable link 188 is situated in the inboard end of the lower portion of the cam surface.

A trip link 214 cooperates with another cam surface, generally designated 216, formed in an enlarged central portion of the second link 194. The trip link and second cam surface cooperate to normally hold the over-center linkage 102 in its stable, upright condition. The trip link 214 has its inboard end pivotally mounted by pin 218 to the central portion of the separable link 188 behind the second link 194 and extends outboard so that its outer end extends beyond the location of the outboard edge of the separable link 188 and of the outboard edge of the container 16. The cam surface 216 has a lower detent portion 220 in which a follower 222, rotatably mounted on the central portion of the trip link 214, normally rests when the pack assembly is in its stable position. (The trip link 214 is best seen in this locking position in FIG. 8 wherein the over-center link 102 is locked so as to prevent pack deployment when the pack assembly is being raised with the door under normal conditions.) An inwardly extending flange 224 is mounted on the inner side of the door 10 at a location above the floor and below the location of the outboard end of the trip link 214. As the door is raised when the pack assembly is locked into the floor fittings 124 and 126, the flange 224 engages the outboard end of the trip link 214 and thus moves it out of engagement with the detent portion 220 of the cam surface 216 and move it into the upper portion of the cam surface 216, allowing the upper ends of the separable link 188 and the second link 194 to move apart. The links are caused to move apart by the weight of the container resting on the shaft 200 at the upper end link 94. As the links move apart, the container is moved outboard, thereby shifting or moving its center of gravity 228 outboard from a vertical line through the shaft 200 that couples the upper end of the second link to the inboard extension on the cam member 196.

Referring to FIG. 16a, a sideward extension 230 (shown also in FIGS. 1, 2 and 2a) on each of the plate portions 110 of the girt bar assembly are caused to move inwardly as the door rises so that they abut the outboard portion of the upright stop member 132 on each of the floor fittings 124 and 126. This sideward extension 230, which extends slightly inboard and then transversely relative to the door and the container assembly as viewed in FIGS. 2 and 2a, has been omitted in many of the intermediate views for clarity of illustration. The transverse extension cooperating with the upright stop 132 prevents the container from falling inwardly relative to the door opening after it is released from the door.

As the door 10 clears the upper end of the container 16 during its upward traverse, shown in FIGS. 17 and 18, the container rotates in a counterclockwise direction about the shaft 200 interconnecting the cam member 196 and the second link 194 while the cam follower 206 traverses toward the upper end of the vertical cam portion 210. The trip cam surface 216 is sufficiently large so as to allow a relatively wide separation between the cam follower 206 and the shaft 200 as the container 16 rotates outwardly toward the door opening 12 in the fuselage 14. As the container 16 rotates, the center of gravity 228 also moves outboard. When the follower 206 reaches the upper end of the vertical cam portion 210, the trip cam surface 216 is so sized as to prevent further separation of the cam follower 206 from the shaft 200. Thus the coaction of the trip link 214, the trip link follower 222 and the trip cam surface 216 are such as to lock the separable link 188 and the second link 194 in their respective positions shown in FIG. 18. However, at this point the cam follower 206 engages the cam portion 212 formed by flange 204 on the cam member 196. Since the center of gravity 228 is located outboard from the shaft 200, the entire container and deployment assembly will rotate solely about the pins 200 as the cam follower 206 traverses the cam portion 212 to a position where the center of gravity is positioned outboard from the bottom portion of the girt bar assembly 100 as shown in FIG. 19.

Figure 20:
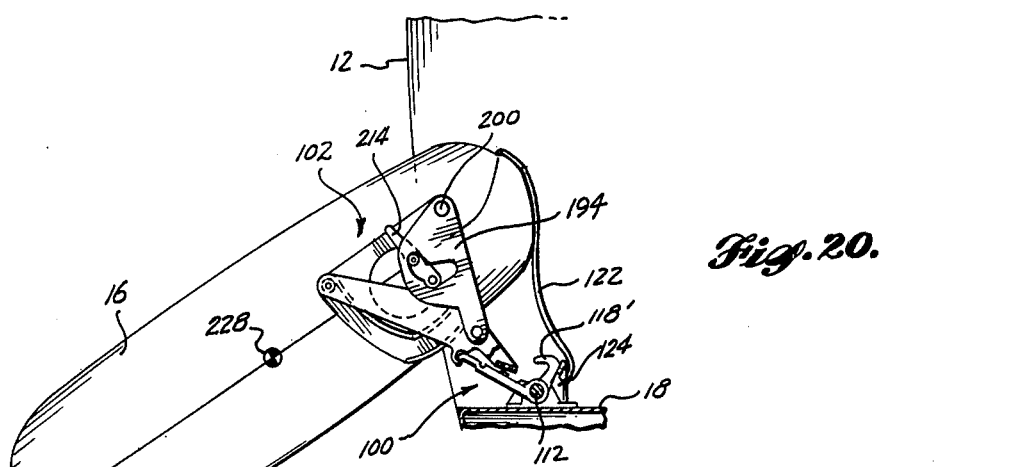
FIG. 20 is a view similar to FIG. 19 showing the container in a nearly fully deployed position wherein the container is being separated from the lower portion of the girt bar assembly.

Since the bottom portion of the girt assembly 100 is rotatably mounted on the girt bar torque tube 112 by bearings 114 (FIGS. 2 and 2a) and since the girt bar torque tube 112 is rigidly affixed to the floor by the rotatable latch members 138 in the floor fittings 124, the container 16 will thereafter rotate in a counterclockwise direction about the girt bar torque tube 112 and fall outwardly to and beyond the position shown in FIG. 20. As the container swings outwardly, the plate portion of the girt bar, which is normally upright, rotates to a position approaching parallelism with the passenger deck 18. Thus the escape slide container has swung to a position where the upper end of the container is located outside of the door opening 12 in the fuselage 14 and lower than the passenger deck 18.

Figure 22:
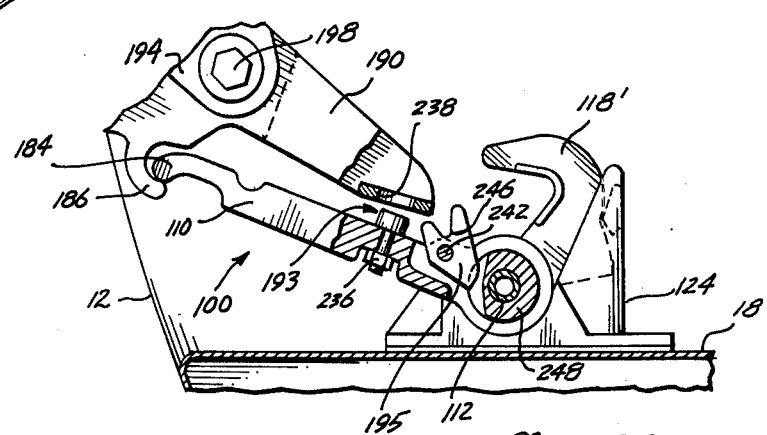
FIG. 22 is a view similar to FIG. 21 showing the over-center linkage separating from the bottom portion of the girt bar assembly in correspondence with the position of the over-center linkage as illustrated in FIG. 20.
Figure 23:
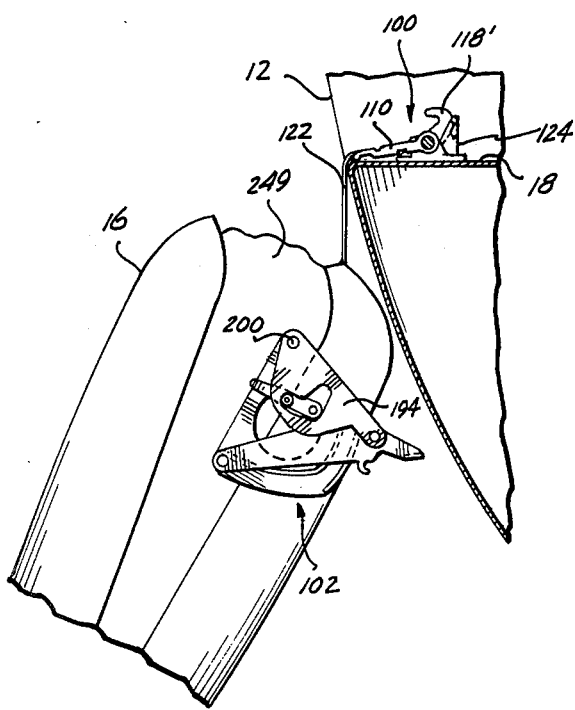
FIG. 23 is a view similar to FIG. 20 showing the container fully deployed out the fuselage door and connected to the bottom portion of the girt bar assembly via a girt strap.

At this point of the container's swinging motion during deployment, the separable link 188 begins to separate from the plate portion 110 of the girt bar assembly 100. This separation is made possible by a unique self-releasing coupling mechanism that is actuated by rotation of the girt bar assembly 100 about the girt bar torque tube 112 during deployment of the slide. Referring now to FIGS. 2, 2a and 21 (the latter of which illustrates the container 16, the over-center linkage 102 and the girt bar assembly in the armed mode and positioned substantially as also shown in FIG. 16), the tubular portion 108 of the girt bar assembly 100, as previously mentioned, is rotatably mounted by bearings 114 (FIG. 2a) on the girt bar torque tube 112. The self-releasing coupling of the separable link 188 and the plate portion 110 maintains the girt bar assembly as an integral unit when the container is upright prior to deployment. The protrusion 193 is formed by the head of a bolt 234 inserted through a bore in the plate portion 110 of the girt bar assembly and fastened in place with a nut 236. The aperture 238 in the downwardly extending flange of the separable link 188 is formed in the transverse member 192 that abuts the inboard surface of the plate portion 110 of the girt bar assembly when the container is in its upright, undeployed position. Cam follower 195 is mounted for rotation about an axis parallel to the girt bar torque tube 112 on a shaft 242 affixed by brackets 244 mounted on the plate portion 110 of the girt bar assembly. The cam has a bight 246 into which the transverse flange member 192 of the separable link 188 is inserted. The opposite follower end of the cam follower 195 rides on a cam 248 affixed to the girt bar torque tube 112. The cam 248 is essentially circular but has an outwardly facing section 250 of reduced diameter. The cam follower 195 bears on the circular surface portion of the cam 248 when the container and the plate portion 110 of the girt bar assembly are upright and continues to do so until the plate portion 110 of the girt bar assembly has rotated relative to the girt bar torque tube 112 through about a 70° angle from its upright position. Thereafter, the follower end of the cam follower 195 meets the reduced diameter portion 250 of the cam as shown in FIG. 22 allowing the cam follower to rotate about its mounting shaft 242. As the cam rotates, the transverse member 192 of the separable link 188 is released by the cam follower 195 and allowed to disengage from the bolt head 234. The separable link 188 can then pivot about the upward extension 184 on the plate portion 110 of the girt bar assembly. Since the outboard end of the plate portion 110 is positioned adjacent the door opening 12, the container is then released from the lower portion of the girt bar assembly 100 and allowed to drop downwardly from the door opening 12 on the outboard side of the fuselage 14, as shown in FIG. 23.

The girt strap 122, as previously mentioned, is connected to the plate portion 110 of the girt bar assembly 100 and to the escape slide packed within the slide container 16, thus providing a flexible connection between the girt bar and the separated slide allowing the pack and slide to swing inwardly toward the aircraft fuselage and contact it after deployment. The container is then separated into its outboard portion 16a and the cover portion 16b by conventional container release means (such as ripcord actuated pin latches), deploying the slide 249 from the container 16.

Referring now to FIGS. 24 and 25, an alternate embodiment of the locking and unlocking handle and the hand-operated actuating mechanism for arming and disarming the pack assembly is illustrated. In FIG. 25, the mechanism is shown in the disarmed position. The mechanism is similar in many respects to that previously described in conjunction with FIGS. 1, 3, 6 and 10. In FIGS. 24 and 25, like parts are identified with the same numerals primed for ease of explanation and comparison. Those parts different from the first-described embodiment are identified with new reference numerals. In FIG. 24, the mechanism is shown in the armed condition wherein the arming handle 78' is rotated to its downward position, rotating its mounting shaft 80' in a clockwise direction (when viewed from the left). Through link 82', shaft 86' and link 88', the latch hook 118 (not shown) is released from the latch pins on the door. In this embodiment, there are two interior door opening handles 252 and 253. Both handles are mounted for rotation on handle mounting shaft 254, which is in turn mounted in bearings 256 attached to fuselage structure (not shown). Shaft 254 corresponds to shaft 42 of the prior embodiment. Each of the door unlocking and opening handles 253 and 252 have two parallel arms, each of which is constructed to rotate about the shaft. The emergency opening handle 252 has a boss 258 on the upper end of its rotatable left arm that is rotatably mounted on the shaft 254. The corresponding adjacent arm of the normal (nonemergency) door opening handle 253 is rotatably mounted on the shaft 254 adjacent the boss 258 of the normal opening handle 253. The upper end of the left-hand arm of the normal opening handle 253 carries a boss 266 that is rotatably mounted on the shaft 254. The adjacent left-hand arm of the emergency opening handle is rotatably mounted on the left-hand boss 266. Thus both handles are mounted for rotation about axes coincident with the rotational axis of shaft 254.

The shaft 254 is splined between the end mounting arms of the handles 253 and 252. A mating splined follower 260 is slidably mounted on the shaft splines for movement in an axial direction along the shaft 254. The follower 260 has keys 262 and 264 that can mate with corresponding grooves in the boss 258 of the emergency opening handle 252 and boss 266 of the normal opening handle 253. A follower actuating bell crank 268 is pivotally mounted on a fixed shaft 270 (in turn affixed to fuselage structure not shown). The shaft 270 is mounted transversely to the axis of handle mounting shaft 254. The lower arm of the bell crank 268 carries a pin 272 which extend inwardly and mates with an annular groove 274 in the periphery of the splined follower 260. As the bell crank is rotated about its mounting pin 270, the splined follower 260 can be moved back and forth on shaft 254 so as to engage keyways in the emergency opening handle boss 258 or the keyway in the normal handle boss 266.

The bell crank 268 also carries two transverse arms 276 and 278 positioned above the location of the handle mounting shaft 254. As the bell crank 268 is rotated to position the follower 260 in one or the other of bosses 258 and 266, the arms 276 and 278 drop into vertical slots 280 and 282 provided in upward extensions respectively on the lefthand arm of the normal opening handle 253 and the right-hand arm of the emergency opening handle 252. Thus as key 262 on the follower 260 is positioned in the keyway of the emergency handle boss 258, the arm 276 is positioned in the slot 280 to hold the normal opening handle in a fixed position. Thus the normal opening handle 253 is held in a fixed position so that it cannot rotate while the emergency opening handle 252 is free to rotate. As the latter is rotated, the boss 258 drives the splined follower 260 so as to rotate the shaft 254 and unlock and open the door, leaving the container attached to the floor and prepared for deployment in the manner described in connection with the first embodiment.

The bell crank 268 is actuated by a link 286 coupled between an upper arm of the bell crank 268 and an arm 288 affixed to the arming handle shaft 80'. As the arming handle 78' is pulled upwardly to its armed position, the shaft 80' is rotated, lifting link 286 to rotate the bell crank 268 in a clockwise direction to the position shown in FIG. 25, as the bell crank is rotated, the splined follower 260 is shifted so that the opposite key 264 of follower 260 engages the keyway in the normal handle boss 266, arm 276 is disengaged from the slot 280 in the normal opening handle, and the arm 278 is engaged with the slot 282 on the emergency opening handle 252. Thus in the unarmed mode, the emergency opening handle 252 cannot be moved while the normal opening handle 253 will rotate the shaft 254 through the follower 260 to shift link 56' to unlock the door and cause an upward traverse of the door with the slide container attached to the door.

The foregoing alternate embodiment of the actuating handle mechanism has the advantage of providing a separate handle for opening the door under emergency conditions to deploy the safety slide. The separate handle is preferably labeled with the legend "Emergency Opening Handle", or some other legend or handle grip configuration, so that it will not be inadvertently manipulated to open the door without first disarming the escape slide deployment mechanism under normal operating conditions. Otherwise, the actuating mechanism operates in substantially the same manner as that previously described.

Figure 26:
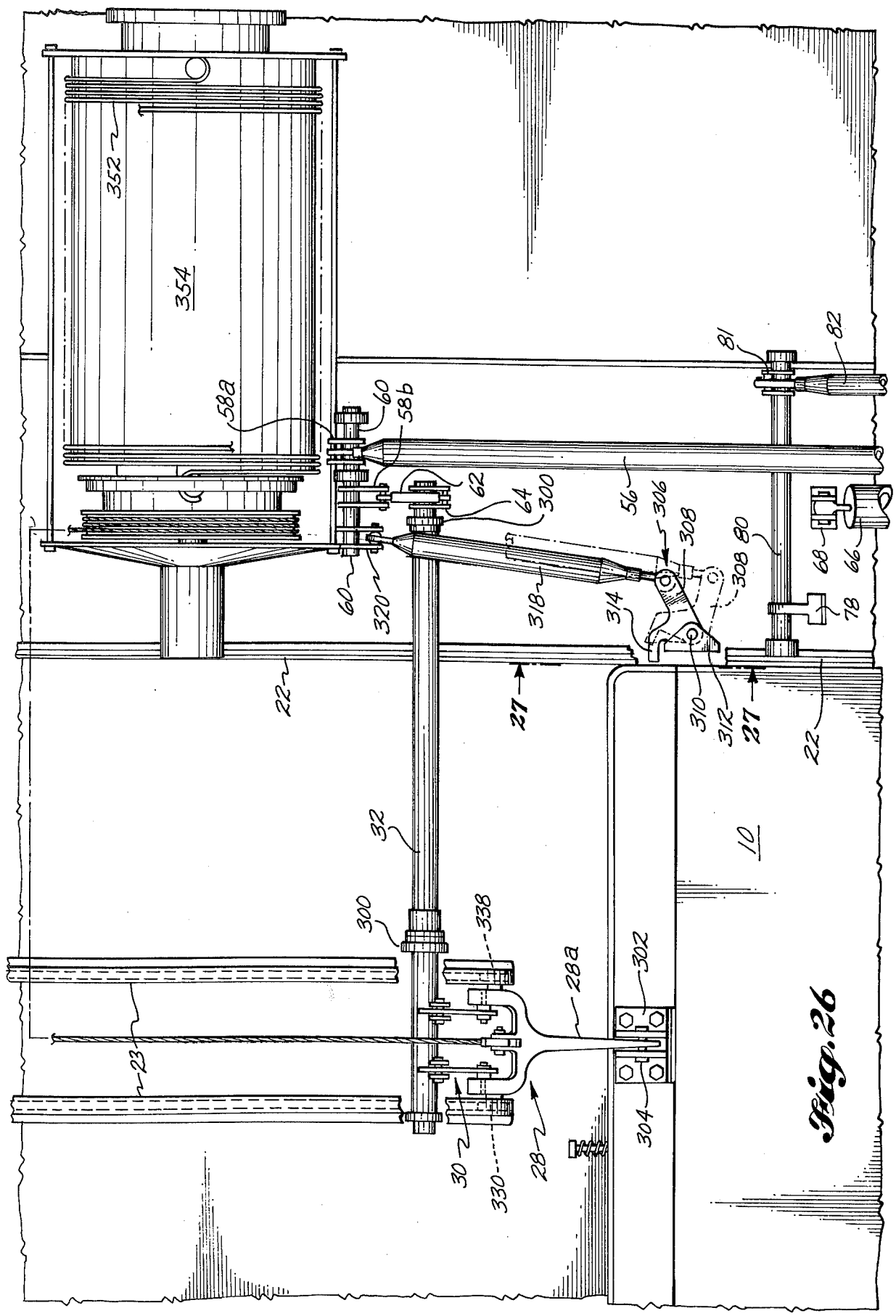
FIG. 26 is an enlarged view of the upper portion of the door opening mechanism, the carrier and plugging and unplugging mechanism, and the latch mechanism on the side of the door similar to that shown in the upper portion of FIG. 1.
Figure 27:
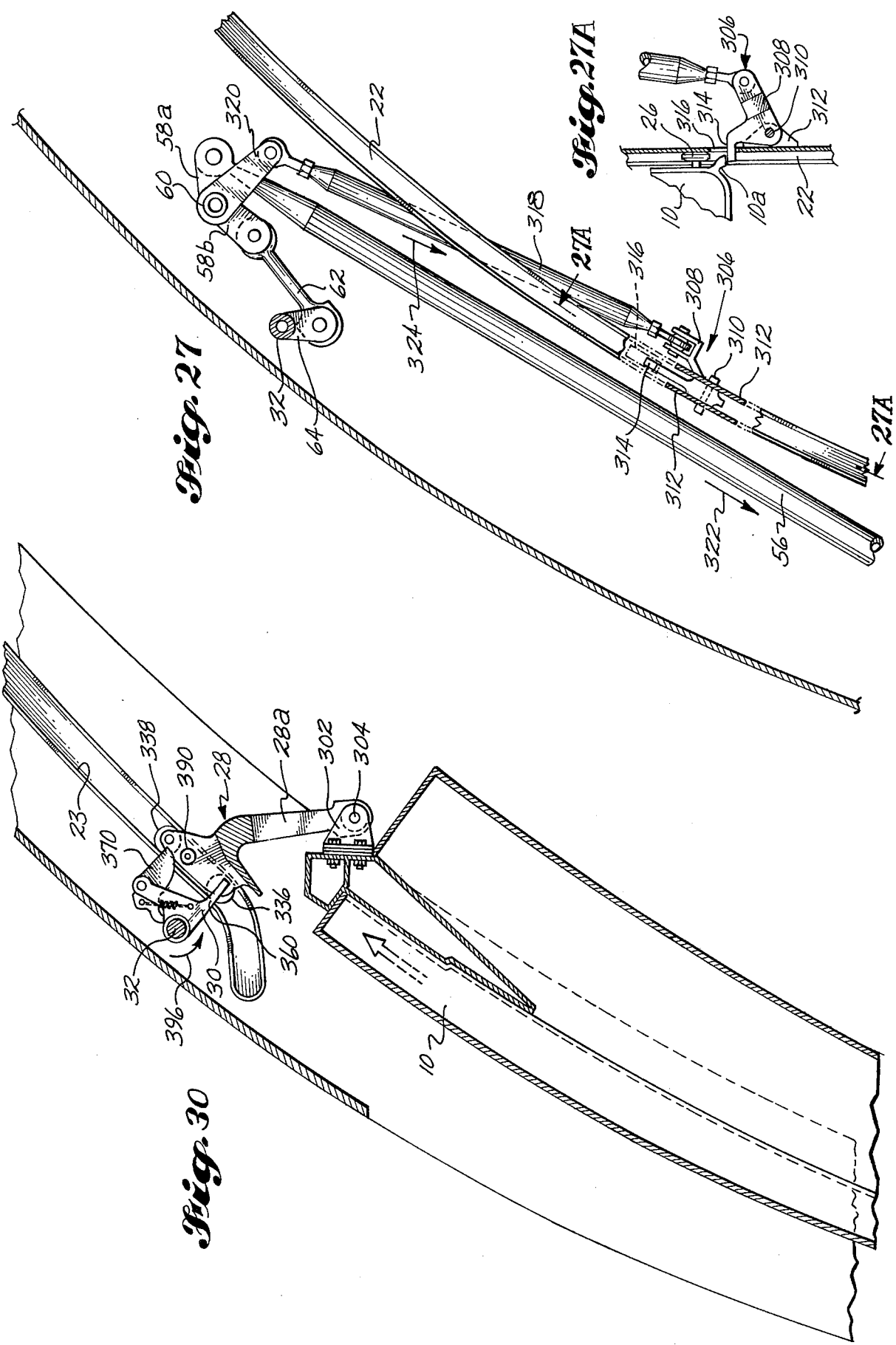
FIG. 27 is a side view in partial cross-section of FIG. 17 taken along section line 18—18, omitting the side door track.

Referring now to FIGS. 26 and 27, the upper portion of the manually actuated opening and closing mechanism, along with the locking and unlocking mechanism coupled to the carrier 28 is coupled by the link 56 to the interior door opening handle 40 via shaft 42 and link 54 (FIG. 1). The upper end of the link 56 is coupled to an arm 58a on shaft 60 in turn rotatably mounted to the fuselage by conventional means. A second arm 58b is coupled to a link 62 which in turn is pivotally coupled to an inwardly extending arm 64 affixed to the locking and unlocking shaft 32. Arms 58a and 58b in combination with the idler shaft 60 function as a bell crank to transmit linear motion of the link 56 through the link 62 and the arm 64 into rotary motion in the locking and unlocking shaft 32. The locking and unlocking shaft 32 is rotatably mounted by bearings 300 to the fuselage in a conventional manner. The locking and unlocking mechanism 30 is affixed to the shaft 32 at a location immediately over the location of carrier 28. The construction and operation of the locking and unlocking mechanism 30 will be described in further detail in conjunction with FIGS. 29, 30 and 31. The carrier 28 has laterally extending followers 330 and 338 that ride in the laterally spaced sections of the upper track 23 that are positioned above the central upper portion of the door 10. A downwardly extending arm 28a integral with the carrier extends below the upper edge of the door 10 and is pivotally coupled to a bracket 302 in turn affixed to the upper portion of the door with conventional fasteners by a pin 304. The track 23 extends upwardly along the fuselage from a position located immediately above the upper protion of the door.

A positive acting safety latch generally designated 306 locks the door in its open position when the door opening handle 40 is in its closed position as shown in FIG. 3. Referring to FIGS. 26, 27 and 27A, the safety latch 306 comprises an arm 308 pivotally mounted by a pin 310 to a bracket 312 fixed to the fuselage adjacent the upper side of the door 10. The pin 310 is oriented in the bracket 312 substantially perpendicular to the fuselage so as to rotate the latch arm 308 in a plane that is oriented substantially parallel to the fuselage and to the door when in its closed position. A locking arm 314 is affixed to the latch arm 308 and extends into an opening in the side of the door right track 22 the latch mechanism 306 is in its latched condition. When the door is in its up position as shown in FIG. 27A, the bottom portion of the door is positioned above the locking arm 314. A stop arm 10a extends sidewardly and downwardly from the lower right hand corner of the door into the track below the follower 26. When the door opening handle 40 is in its closed position (as shown in FIG. 3), the locking arm 314 extends through the opening 316 and blocks the path of both the follower 26 and the stop arm 10a on the door. When the door opening handle 40 is moved to its open position (as shown in FIG. 6), the locking arm is retracted to allow the door and follower 26 to move past the location of the locking arm 314. After the door is raised above the position of the latching mechanism 306 and the door handle 40 is returned to its closed position (as shown in FIG. 3), the locking arm moves into the track in the path of the stop arm 10a, and prevents the door from moving downwardly, thus holding the door in its open position above the door opening in the fuselage.

The latch arm 308 is pivotally coupled to a latch link 318 that extends upwardly from the latch arm and in turn is pivotally coupled to an inwardly extending arm 320 affixed to the idler shaft 60. When the door opening handle 40 (FIG. 3) is rotated upwardly to its door opening position (as shown in FIG. 6), the link 56 is pulled downwardly in the direction of arrow 322 (FIG. 27). As this occurs, the idler shaft 60 is rotated in a clockwise direction as viewed in FIG. 27, causing the latch link 318 to move downwardly in the direction of arrow 324. The downward movement of latch link 318 rotates the latch arm 308 in a clockwise direction as viewed in FIGS. 26 and 27A to the position shown in dotted outline, also rotating the locking pin 314 in a clockwise direction and retracting it from the recess 316 in the track 22. Because of the orientation of the arm 320 on the idler shaft 316, the downward movement of latch link 318 occurs very quickly upon a small movement of the actuating link 56, thus removing the latch pin 314 from the door after the door opening handle 160 has moved only a small distance from its closed position as shown in FIG. 3 toward its open position as shown in FIG. 6.

Figure 28:
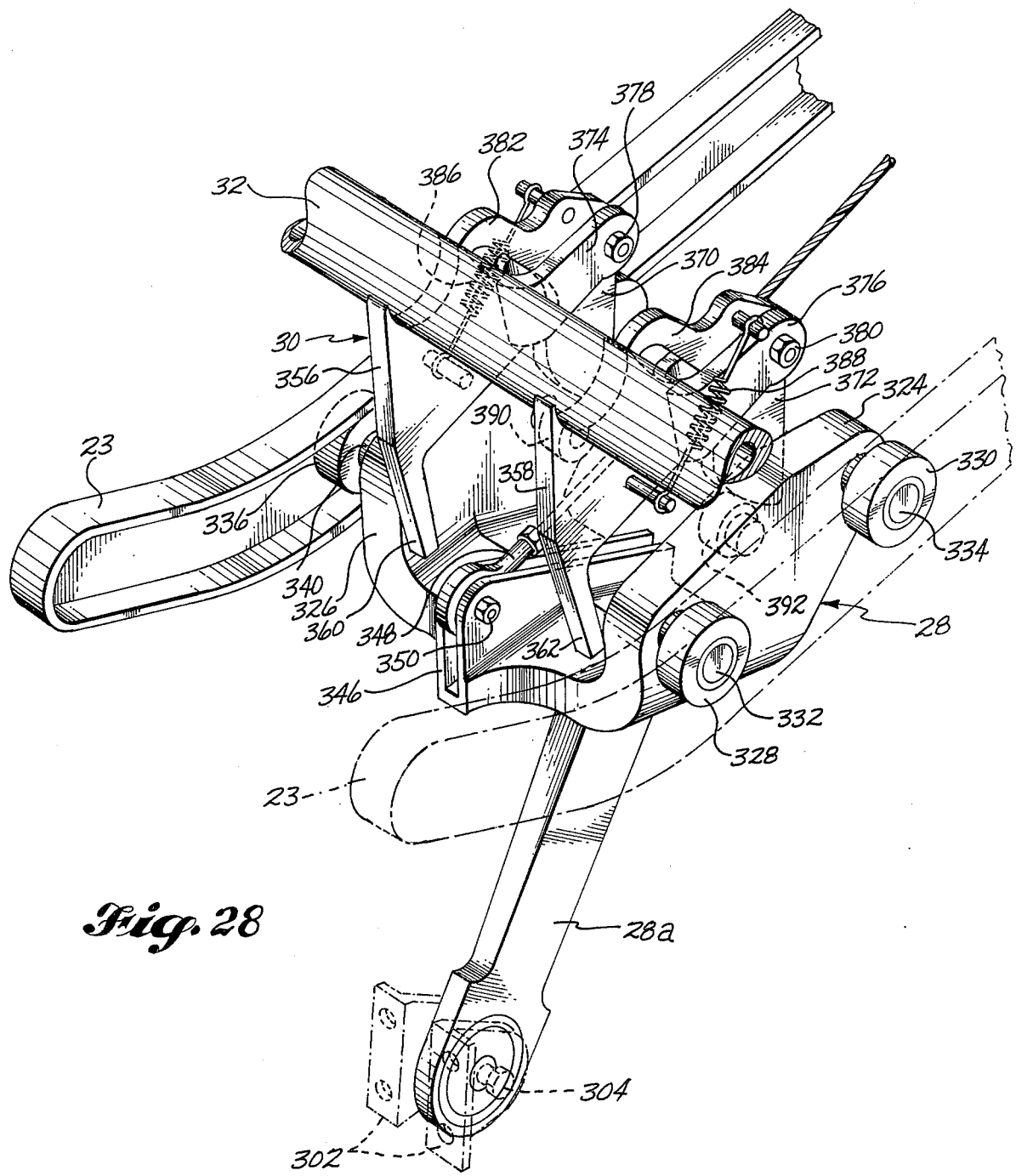
FIG. 28 is a greatly enlarged isometric view of the carrier, the plugging and unplugging mechanism, and a portion of the upper track.

Referring now to FIG. 28, the carrier 28 and the locking and unlocking mechanism 30 is shown in greatly enlarged detail adjacent the bottom portion of the upper or overhead tracks 23. Above the downwardly extending arm 28a, the carrier 28 spreads laterally into a yoke-like member having two upwardly extending, spaced arms 324 and 326 positioned adjacent the mutually opposing sides of the spaced sections of the upper track 23. Followers 328 and 330 are mounted on shafts 332 and 334, respectively affixed to one of the upright arms 324. The followers 328 and 330 ride in one section of the track 23. A second set of followers 336 and 338 (follower 338 can be seen in phantom outline in FIG. 26) are mounted respectively on a first shaft 340 and a second shaft (not visible in FIG. 28), both affixed to the other arm 326 of the yoke-like carrier 28. The followers 336 and 338 ride in the other section of the track 23. At a location intermediate the upstanding arms 324 and 326, the carrier has an upright flange 346. An eye bolt 348 is pivotally coupled by a pin 350 to the upright flange 346. The eye bolt is affixed to a flexible cable 352 that extends upwardly adjacent the path of the tracks 23 through a plurality of sheaves (not shown) to a spring biased counterbalance mechanism 354 (shown in FIG. 26). The counterbalance mechanism provides a counterbalancing force substantially equivalent to the weight of the carrier and the door, thus allowing the door to be manually raised in its overhead traverse even though it would otherwise be difficult to do so without a powered lift mechanism or other power assist.

The locking and unlocking mechanism 30 (FIG. 28) has two spaced flanges 356 and 358 affixed to the locking and unlocking shaft 32 and extending downwardly toward the carrier 28. The flanges 356 and 358 are positioned in spaced relationship within the upright arms 324 and 326 of the carrier. Opening arms 360 and 362, integral with the flanges 356 and 358, extend downwardly toward the base of the yoke-like portion of the carrier. The opening arms 360 and 362 abut the rollers 390 and 392 mounted on the upwardly extending arms 324 and 326. The functional interrelationship of the opening arms 360 and 362 and the rollers 390 and 392 will be explained below in conjunction with FIGS. 29 through 31. Closing arms 370 and 372 are pivotally mounted on inwardly extending yokes 374 and 376 integral with the flanges 356 and 358 affixed to the locking and unlocking tube 32. The closing arms 370 and 372 are pivotally mounted on the inwardly extending yokes 374 and 376 by pins 378 and 380, respectively, which are oriented substantially parallel to the locking and unlocking shaft 32. Each of the closing arms 370 and 372 carry upwardly and outwardly extending stop arms 382 and 384 whose outer and upper ends abut the inwardly facing surface of the flanges 356 and 358 to limit the pivotal movement of the closing arms 370 and 372 in the counterclockwise direction (as viewed in FIG. 28). The closing arms 370 and 372 are biased toward the stop position by coil springs 386 and 388 attached to appropriately positioned pins mounted respectively on the closing arms and on the flanges 356 and 358. The bottom outwardly facing end portions of the closing arms 370 and 372 contact rollers 390 and 392, which are oriented in opposing relationship and are rotatably mounted on the mutually opposing sides of upright arms 324 and 326 of the yoke-like portion of the carrier 28. The rollers 390 and 392 are spaced inwardly relative to the fuselage from the nuts 364 and 368.

Referring now to FIG. 29, the locking and unlocking mechanism 30 is shown in partial cross-section in its locked position with the carrier 28 positioned in the lower terminal end of the track 23 that extends downwardly and outwardly relative to the fuselage. Although only half of the yoke-like portion of the carrier 28 is illustrated in this and the ensuing FIGURES, the opposing portion of the yoke-like portion and appended mechanism operates identically to the illustrated portion. When the carrier is locked in the lower, outwardly extending end of the track 23, the door 10 is positioned in the door opening and is locked there in a plugged condition. In this position, the pivotally mounted closing arm 370 is bearing against the roller 390 to hold the carrier 28 in its locked position in the terminal portion of the track 23. When the door handle 40 is rotated from its closed and locking position (FIG. 3) to its door opening position (FIG. 6), the locking and unlocking bar 32 is rotated in a counterclockwise direction as shown in FIGS. 29 and 30 by arrow 396. As the locking and unlocking shaft 32 rotates in a counterclockwise direction, the opening arm 360 is rotated upwardly in a counterclockwise direction from the position shown in FIG. 29 to the position shown in FIG. 30. At the same time the closing arm 370 is moved in a counterclockwise direction upwardly and out of the path of roller 390, allowing the carrier 28 to move out of the terminal portion of the upper track 23 into the upwardly extending portion of the track 23 under the urging of the counterbalance mechanism coupled to the carrier. If the force on the counterbalance mechanism is insufficient to move the carrier out of the terminal portion of the upper track, the opening arm 360 can be rotated sufficiently far so that it contacts the outer side of the roller 390. Thus as the door opening handle 40 is moved upwardly to rotate the shaft 32 in a counterclockwise direction, the opening arm can exert a force on the roller 390 and thus push the carrier out of the terminal portion of the track 23 into the upwardly extending portion so that the door can begin its upward traverse along the track 23 to its position overhead the fuselage door opening. It is normally contemplated, however, that the force exerted on the counterbalance cable coupled to the eye bolt 343 on the carrier will be adequate to always maintain the roller 390 in contact with the outer cam shaped, outer surface of the closing arm 370. Thus under normal conditions there is no need for the carrier to be forced out of the terminal portion of the track 23 by the opening arm 360. However, under extraordinary circumstances, for example where the structure supporting the door tracks is deformed or where the fuselage is warped so that the door binds in its tracks, the opening arm 360 can function to unlock and unplug the door from the fuselage door opening so that it can be manually raised to its overhead open position.

When it is desired to close the door, it is first manually lowered against the force exerted by the counterbalance mechanism 354. The inner side of the closing arm 370 encounters the roller 390 and pivots to a position shown in dotted outline in FIG. 31 to allow the roller 390 to move past the location of the closing arm 370. After the roller 390 moves past the closing arm 370, the closing arm 370 returns to its stopped position by the bias of spring 386. Thus the locking and unlocking mechanism 30 is in readiness to move the carrier 28 to its locked position in the lower, terminal portion of the track 23. When a crew member is ready to plug the door 10 in the fuselage opening, the interior door handle 40 is swung downwardly from the position shown in FIG. 6 and returned to the locked position as shown in FIG. 3. As this occurs, the locking and unlocking shaft 32 is rotated in a clockwise direction, causing the locking and unlocking mechanism 30 to rotate so that the closing arm 370 bears against the roller 390, thus urging the carrier 28 in the direction of arrow 398 into the lower, terminal portion of the track 23 and returning it to the position shown in FIG. 31. As the carrier comes to rest in the terminal portion of the track 23, the door is again plugged in the fuselage opening.

The present invention has been described in relation to a preferred embodiment and an alternate embodiment for the actuating mechanism. One of ordinary skill, after reading the foregoing specification, will be able to effect various alterations, substitutions of equivalents, and other changes to the invention without departing from the broad concepts disclosed herein. For example, one of ordinary skill will understand that the escape slide deployment linkage arrangement as disclosed will still function to deploy the container even though the passenger deck floor is not horizontally oriented. The linkage is so contructed in the preferred embodiment to move the center of gravity of the container outboard of a vertical line through the pin 200 even when the floor is tilted (that is, slopes downwardly from the door opening) at an angle of at least 12° to 15°. As another example, the upper latch member 172 can be modified to allow replacement or removal of the container from the door when the door is closed, rather than raising the door as is necessary with the disclosed embodiment of the latch member to permit easier removal of the container would require that the U-shaped member be rotatable to allow outward movement of the pack with means for preventing rotation of the member under normal conditions. It is therefore intended that the scope of protection granted by Letters Patent hereon be limited only by the definition contained in the appended claims and equivalents thereof.

What is claimed is:

1. In a door system for an aircraft including a fuselage having a door opening, a floor adjacent the bottom of said door opening, a door and means mounting the door for upward and downward movement between a closed position and an open position, locking means for holding said door in said closed position, an escape slide container normally attached to said door and coupling means for releasing said container from said door and for attaching said container to said floor for deployment through said door opening, improved actuating mechanism for closing and opening said door and for arming and disarming said coupling means comprising:

a first interior handle mounted on said fuselage for swinging movement between a first and second position, said first handle operably associated with said locking means to respectively lock and unlock said door upon movement of said first handle between said first and second positions, a second interior handle mounted on said fuselage for swinging movement between first and second positions for respectively arming and disarming said coupling means, a first exterior handle mounted on said fuselage for swinging movement between first and second positions, and means for coupling said first exterior handle to said first interior handle to simultaneously move said first interior and exterior handles between respective ones of said first and second positions, and a second exterior handle mounted on said fuselage for swinging movement between first and second positions, and means coupling said second exterior handle with said second interior handle to simultaneously move said second handles between respective ones of said first and second positions.

2. The improved mechanism of claim 1 further comprising:
guard means associated with said first interior handle and mounted on said fuselage for swinging movement toward and away from a position blocking manual access to said first interior handle, and means coupling said guard means to said second interior handle for movement to said blocking position when said second interior handle is in its first position.

3. The improved mechanism of claim 2 wherein said guard means is further mounted for manual movement away from said blocking position when said second interior handle is in said first position.

4. The improved mechanism of claim 1 wherein said first and second exterior handles are mounted flush with the exterior surface of said fuselage when said exterior handles are in said first positions, said second exterior handle being constructed and mounted relative to said first exterior handle so that said second exterior handle prevents grasping of said first exterior handle until said second exterior handle is moved from its first position to its second position.

5. The improved mechanism of claim 1 further comprising:
a third interior handle associated with said first interior handle and movable between first and second positions, said first and third interior handles being in said first position when said door is closed, said third interior handle operably associated with said locking means to respectively lock and unlock said door upon movement of said third interior handle between said first and second positions, and
means coupled to said second interior handle for selectively locking said first and third interior handles in said first position, said third interior handle being locked in its first position when said second interior handle is in said first position, said first interior handle being locked in its first position when said second interior handle is in its second position.

6. In a door system for an aircraft fuselage having a door opening, a door and lower track means for mounting the door for upward and downward sliding movement between a closed position and an open position spaced above said door opening, said door when in said closed position plugging said door opening, said door having follower means thereon associated with said lower track means and cooperating with said lower track means when said door is opened to move said door inwardly relative to said door opening, to unplug said door from said door opening and to position said door for upward traverse to a location over said door opening, an improved apparatus for suspending the upper end of said door and for plugging and unplugging said door from said door opening comprising:
upper track means mounted on said fuselage above said door opening, said upper track means having an upper portion extending upwardly from a first location adjacent the upper portion of said door opening and a second location spaced upwardly from said first location, said upper track means having a terminal portion curving outwardly toward said fuselage from said first location;
a carrier having followers thereon operatively associated with and guided by said upper track means, said carrier including an arm affixed to and extending downwardly from said carrier and means for pivotally attaching said arm to the upper portion of said door,
a rotatable member mounted for rotation on said fuselage about an axis spaced from and oriented transversely to said upper track means, said rotatable member and said carrier including first means for coupling said rotatable member to said carrier for moving at least a portion of said carrier from a rest position in the terminal portion of said upper track means into the upper portion of said upper track means solely in reaction to the rotational movement of said rotatable member, and for releasing said rotatable member from said carrier for upward movement of said carrier in said upper portion when said carrier has reached a location adjacent the junction of said terminal portion and said upper portion of said upper track means.

7. The apparatus of claim 6 further comprising:
first manually actuated handle means mounted for swinging movement on said fuselage and movable between a first position and a second position,
first linkage means for coupling said first manually actuated handle means to said rotatable member for moving said rotatable member between a first and a second position responsive to movement of said first manually actuated handle means between said first and second positions thereof, respectively, said rotatable member in said first position cooperating to lock said carrier in said terminal portion of said upper track means, said rotatable member when moving from its first position to its second position causing said carrier to transit from the terminal portion of said upper track means, said first means releasing said carrier for upward movement in said upper track means when said rotatable member is in said second position.

8. The apparatus of claim 7 further comprising:
latch means mounted on said fuselage and cooperating with said door when said door is in its open position for latching said door in said open position located above said fuselage door opening when said rotatable member is in its first position, said latch means movable between a latched position and an unlatched position, and second linkage means coupling said latch means to said first manually actuated handle means for moving said latch means between respective ones of said latched and unlatched positions as said first manually actuated handle means is moved between said first and second positions.

9. The apparatus of claim 8 wherein said latch means comprises:
means defining a latch stop on said door and a rotatable latch member having a pin movable into and out of the path of said latch stop as said door is raised and lowered, said rotatable latch member being positioned in the path of said latch stop when said first manually actuated handle means is in said first position to prevent lowering of said door.

10. In a door system for an aircraft fuselage having a door opening, a door and lower track means for mounting the door for upward and downward sliding movement between a closed position and an open position spaced above said door opening, said door when in said closed position plugging said door opening, said door having follower means thereon associated with said lower track means and cooperating with said lower track means when said door is opened to move said door inwardly relative to said door opening to unplug said door from said door opening and to position said door for upward traverse to a location over said door opening, an improved apparatus for suspending the upper end of said door and for plugging and unplugging said door from said door opening comprising:

upper track means mounted on said fuselage above said door opening, said upper track means having an upper portion extending upwardly from a first location adjacent the upper portion of said door opening and a second location spaced upwardly from said first location, said upper track means having a terminal portion curving outwardly toward said fuselage from said first location;

a carrier having followers thereon operatively associated with and guided by said upper track means, said carrier including an arm affixed to and extending downwardly from said carrier, and means for pivotally attaching said arm to the upper portion of said door; and, a rotatable member mounted for rotation on said fuselage about an axis spaced from and oriented transversely to said upper track means, said rotatable member being movable between a first and a second position, said rotatable member in said first position cooperating to lock said carrier in said terminal portion of said upper track means, said rotatable member when moving from its first position to its second position causing said carrier to transit from the terminal portion of said upper track means and to release said carrier for upward movement in said upper track means when said rotatable member is in said second position, said rotatable member and said carrier including first means for releasably coupling said rotatable member to said carrier for transiting said carrier from a rest position in the terminal portion of said upper track means toward the upper portion of said upper track means, and second means for moving said carrier from a location adjacent the terminal portion of said upper track means into said terminal portion of said upper track means as said rotatable member moves from said second position to said first position and for locking said carrier in the terminal portion of said upper track means when said rotatable member is in said first position.

11. The apparatus of claim 10 wherein said first means comprises:

a first arm extending from said rotatable member toward said carrier and oriented transversely relative to the rotational axis of said rotatable member, and a first abutment member on said carrier cooperating with said first arm to move said carrier as said rotatable member rotates and swings said arm about the rotational axis of said rotatable member.

12. The apparatus of claim 11 wherein said second means comprises:

a second arm extending from said rotatable member toward said carrier and oriented transversely relative to the rotational axis of said rotatable member and spaced from said first arm, and a second abutment member on said carrier spaced from said first abutment member, said second abutment member cooperating with said second arm to move said carrier from adjacent the terminal portion of said upper track means into the terminal portion of said upper track means as said rotatable member rotates from said second position to said first position.

13. The apparatus of claim 12 wherein said second arm is pivotally mounted on said rotatable member for limited swinging movement about an axis substantially parallel to the rotational axis of said rotatable member, said second arm movable between a first position contacting said second abutment member in driving relationship to move said carrier into the terminal portion of said upper track means as said rotatable member is moved from said second position to said first position, and said second arm movable to a second position allowing said second abutment member on said carrier to move past said second arm toward the terminal portion of said upper track means relative to said rotatable member, and means biasing said second arm toward its first position.

14. The apparatus of claim 10 further comprising:

first manually actuated handle means mounted for swinging movement on said fuselage and movable between a first position and a second position, linkage means for coupling said first manually actuated handle means to said rotatable member for moving said rotatable member between said first and second positions of said rotatable member responsive to movement of said first manually actuated handle means between said first and second positions respectively of said first manually actuated handle means.

15. The apparatus of claim 14 further comprising:

latch means mounted on said fuselage and cooperating with said door when said door is in an open position for latching said door in said open position located above said fuselage door opening when said rotatable member is in its first position, said latch means movable between a latched position and an unlatched position; and second linkage means coupling said latch means to said first manually actuated handle means for moving said latch means between respective ones of said latched and unlatched positions as said first manually actuated handle means is moved between said first and second positions thereof.

16. The apparatus of claim 15 wherein said latch means comprises:

means defining a latch stop on said door and a rotatable latch member having a pin movable into and out of the path of said latch stop as said door is raised and lowered said rotatable latch member being positioned in the path of said latch stop when said first manually actuated handle means is in its first position and said door is in said open position to prevent lowering of said door.

* * * * *